(12) United States Patent
McConnell et al.

(10) Patent No.: US 7,893,049 B2
(45) Date of Patent: *Feb. 22, 2011

(54) THIAZOLYL-DIHYDRO-INDAZOLE

(75) Inventors: Darryl McConnell, Vienna (AT); Bodo Betzemeier, Bad Fischau (AT); Thomas Gerstberger, Vienna (AT); Maria Impagnatiello, Vienna (AT); Steffen Steurer, Vienna (AT); Lars van der Veen, Vienna (AT); Ulrike Weyer-Czernilofsky, Baden (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 746 days.

This patent is subject to a terminal disclaimer.

(21) Appl. No.: 11/696,900

(22) Filed: Apr. 5, 2007

(65) Prior Publication Data

US 2008/0081802 A1  Apr. 3, 2008

(30) Foreign Application Priority Data

Apr. 6, 2006  (EP)  ................... 06112304

(51) Int. Cl.
| | |
|---|---|
| *A61K 31/00* | (2006.01) |
| *A61K 31/44* | (2006.01) |
| *A61K 31/445* | (2006.01) |
| *A61K 31/497* | (2006.01) |
| *A61P 43/00* | (2006.01) |
| *C07D 211/32* | (2006.01) |
| *C07D 217/00* | (2006.01) |
| *C07D 279/10* | (2006.01) |
| *C07D 401/00* | (2006.01) |
| *C07D 413/00* | (2006.01) |

(52) U.S. Cl. ................ 514/210.21; 514/228.5; 514/232.8; 514/253.09; 514/307; 514/318; 544/115; 544/364; 546/144; 546/199; 546/275.7

(58) Field of Classification Search ............ None
See application file for complete search history.

(56) References Cited

FOREIGN PATENT DOCUMENTS

| CA | 2579288 A1 | 4/2006 |
|---|---|---|
| WO | 0157008 A1 | 8/2001 |
| WO | 2006040281 A1 | 4/2006 |

OTHER PUBLICATIONS

Golub et al. Science (1999), vol. 286, 521-537.*
International Search Report (Form PCT/ISA/220) for corresponding PCT/EP2007/053093.

* cited by examiner

*Primary Examiner*—Kamal A Saeed
(74) *Attorney, Agent, or Firm*—Michael P. Morris; Philip I. Datlow

(57) ABSTRACT

The present invention encompasses compounds of general formula (1)

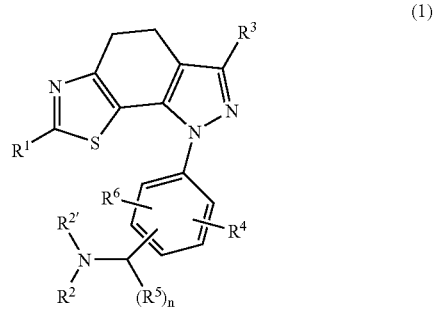

(1)

wherein
$R^1$ to $R^6$ are defined as in claim 1, which are suitable for the treatment of diseases characterized by excessive or abnormal cell proliferation, and the use thereof for preparing a medicament having the above-mentioned properties.

10 Claims, No Drawings

THIAZOLYL-DIHYDRO-INDAZOLE

This application claims priority of EP 06112304, filed Apr. 6, 2006.

The present invention relates to new thiazolyl-dihydro-indazoles of general formula (1)

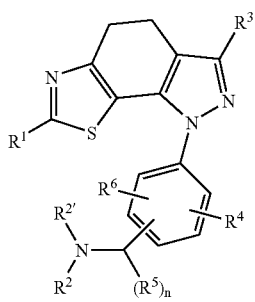

(1)

wherein the groups $R^1$ to $R^6$ have the meanings given in the claims and specification, the isomers thereof, processes for preparing these thiazolyl-dihydro-indazoles and their use as medicaments.

BACKGROUND TO THE INVENTION

A number of protein kinases have already proved to be suitable target molecules for therapeutic intervention in a variety of indications, e.g. cancer and inflammatory and autoimmune diseases. Since a high percentage of the genes involved in the development of cancer which have been identified thus far encode kinases, these enzymes are attractive target molecules for the therapy of cancer in particular.

Phosphatidylinositol-3-kinases (PI3-kinases) are a subfamily of the lipid kinases which catalyse the transfer of a phosphate group to the 3'-position of the inositol ring of phosphoinositides.

They play an important role in numerous cell processes such as e.g. cell growth and differentiation processes, the control of cytoskeletal changes and the regulation of intracellular transport processes. On the basis of their in vitro specificity for certain phosphoinositide substrates the PI3-kinases can be divided into different categories.

DETAILED DESCRIPTION OF THE INVENTION

It has now surprisingly been found that compounds of general formula (1), wherein the groups $R^1$ to $R^6$ have the meanings given below, act as inhibitors of specific cell cycle kinases. Thus, the compounds according to the invention may be used for example for the treatment of diseases connected with the activity of specific cell cycle kinases and characterised by excessive or abnormal cell proliferation.

The present invention relates to compounds of general formula (1)

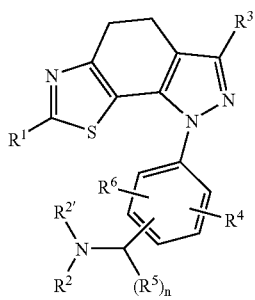

(1)

wherein
$R^1$ is selected from among —NHR$^a$, —NHC(O)R$^a$, —NHC(O)OR$^a$, —NHC(O)NR$^a$R$^a$ and —NHC(O)SR$^a$, and
$R^2$ and $R^{2'}$ in each case independently of one another denote hydrogen or a group selected from among $C_{1-6}$alkyl, $C_{3-8}$cycloalkyl, $C_{6-10}$aryl, 5-10 membered heteroaryl and 3-8 membered heterocycloalkyl, optionally substituted by one or more R$^a$ and/or R$^b$, or
$R^2$ and $R^{2'}$ together with the enclosed nitrogen atom form a heterocycloalkyl or heteroaryl ring, which may optionally contain one or more further hetero atoms, selected from among N, O and S and may optionally be substituted by one or more R$^b$ and/or R$^d$, and
$R^3$ denotes a group selected from among $C_{6-10}$aryl and 5-6 membered heteroaryl, optionally substituted by one or more identical or different R$^c$ and/or R$^b$, and
$R^4$ and $R^6$ each independently of one another denote hydrogen or a group selected from among halogen, —CF$_3$, —OCF$_3$, —CN, —NR$^c$R$^c$, —SR$^c$, —S(O)R$^c$, —S(O)$_2$R$^c$ and —OR$^c$, or $C_{1-3}$alkyl optionally substituted by fluorine, —CN, —NR$^f$R$^f$ and/or —OR$^f$, and
$R^5$ denotes $C_{1-3}$alkyl, or
two R$^5$ together form a $C_{3-8}$cycloalkyl ring or 3-8 membered heterocycloalkyl, and n is equal to 0, 1 or 2, or
$R^2$ with an R$^5$ forms a 4-8 membered heterocycloalkyl ring, or
$R^2$ with a suitable R$^6$ forms a 4-8 membered heterocycloalkyl ring, and
each R$^a$ independently of one another denotes hydrogen or a group optionally substituted by one or more identical or different R$^b$ and/or R$^c$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and
each R$^b$ denotes a suitable group each selected independently of one another from among =O, —OR$^c$, $C_{1-3}$haloalkyloxy, =S, —SR$^c$, =NR$^c$, =NOR$^c$, —NR$^c$R$^c$, halogen, —CF$_3$, —CN, —NC, —NO$_2$, —N$_3$, —S(O)R$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)$_2$NR$^c$R$^c$, —C(O)R$^c$, —C(O)OR$^c$, —C(O)NR$^c$R$^c$, —C(O)N(R$^d$)OR$^c$, —CN(R$^d$)NR$^c$R$^c$, —OC(O)R$^c$, —OC(O)OR$^c$, —OC(O)NR$^c$R$^c$, —OCN(R$^d$)NR$^c$R$^c$, N(R$^d$)C(O)R$^c$, —N(R$^d$)C(S)R$^c$, —N(R$^d$)S(O)$_2$R$^c$, —N(R$^d$)C(O)OR$^c$, —N(R$^d$)C(O)NR$^c$R$^c$, and —N(R$^d$)CN(R$^d$)NR$^c$R$^c$, and
each R$^c$ independently of one another denotes a group optionally substituted by one or more identical or different R$^d$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and
each R$^d$ independently of one another denotes $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl,
optionally in the form of the tautomers, the racemates, the enantiomers, the diastereomers and the mixtures thereof, as well as optionally the pharmacologically acceptable acid addition salts thereof, with the proviso that the following compounds are not included:
N-[1-(4-morpholin-4-ylmethyl-phenyl)-3-pyridin-2-yl-4,5-dihydro-1H-pyrazolo[4,3-g]benzothiazol-7-yl]-acetamide, N-[1-(4-dimethylaminomethyl-phenyl)-3-pyridin-3-yl-4,5-dihydro-1H-pyrazolo[4,3-g]benzothiazol-7-yl]-acetamide, N-{1-[4-(benzylamino-methyl)-2-chloro-phenyl]-3-pyrazin-2-yl-4,5-dihydro-1H-pyrazolo[4,3-g]benzothiazol-7-yl}-acetamide and N-(1-{2-chloro-4-[(1-cyclopentyl-piperidin-4-ylamino)-methyl]-phenyl}-3-pyrazin-2-yl-4,5-dihydro-1H-pyrazolo[4,3-g]benzothiazol-7-yl)-acetamide.

One aspect of the invention relates to compounds of general formula (1A),

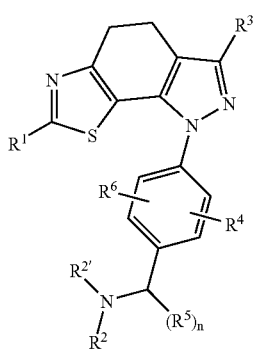

(1A)

wherein the substituents are as hereinbefore defined.

One aspect of the invention relates to compounds of general formulae (1) or (1A), wherein $R^3$ denotes 5-6 membered heteroaryl, optionally substituted by one or more identical or different $R^c$ and/or $R^b$.

One aspect of the invention relates to compounds of general formulae (1) or (1A), wherein $R^3$ denotes unsubstituted pyridyl, particularly pyridin-3-yl.

One aspect of the invention relates to compounds of general formulae (1) or (1A), wherein $R^1$ is selected from among —NHC(O)$R^a$, —NHC(O)O$R^a$ and —NHC(O)N$R^a R^a$.

(A) Aspects relating to $R^1$ (A1) One aspect of the invention relates to compounds of general formula (1) or (1A), wherein $R^1$ denotes —NHC(O)CH$_2$CH$_3$.

(A2) Another aspect of the invention relates to compounds of general formula (1) or (1A), wherein $R^1$ denotes —NHC(O)OCH$_3$ or —NHC(O)OCH$_2$CH$_3$.

(A3) One aspect of the invention relates to compounds of general formula (1) or (1A), wherein $R^1$ denotes —NHC(O)CH$_3$, and $R^2$ and $R^{2'}$ in each case independently of one another denote hydrogen or a group selected from among $C_{3-6}$alkyl, $C_{3-8}$cycloalkyl, $C_{6-10}$aryl, 5-10 membered heteroaryl and 3-8 membered heterocycloalkyl, optionally substituted by one or more $R^a$ and/or $R^b$, or $R^2$ and $R^{2'}$ together form a heterocycloalkyl or heteroaryl ring, which may optionally contain one or more further hetero atoms, selected from among N and S and optionally substituted by one or more $R^b$ and/or $R^d$, and wherein each $R^b$ denotes a suitable group each independently selected from among =O, —O$R^c$, $C_{1-3}$haloalkyloxy, =S, —S$R^c$, =N$R^c$, =NO$R^c$, —N$R^c R^c$, halogen, —CF$_3$, —CN, —NC, —NO$_2$, —N$_3$, —S(O)$R^c$, —S(O)$_2 R^c$, —S(O)$_2$O$R^c$, —S(O)N$R^c R^c$, —S(O)$_2$N$R^c R^c$, —OS(O)$R^c$, —OS(O)$_2 R^c$, —OS(O)$_2$O$R^c$, —OS(O)$_2$N$R^c R^c$, —C(O)$R^c$, —C(O)O$R^c$, —C(O)N$R^c R^c$, —C(O)N($R^d$)O$R^c$—CN($R^d$)N$R^c R^c$, —OC(O)$R^c$, —OC(O)O$R^c$, —OC(O)N$R^c R^c$, —OCN($R^d$)N$R^c R^c$, —N($R^d$)C(O)$R^c$, N($R^d$)C(S)$R^c$, N($R^d$)S(O)$_2 R^c$, —N($R^d$)C(O)O$R^c$, —N($R^d$)C(O)N$R^c R^c$, and —N($R^d$)CN($R^d$)N$R^c R^c$, and each $R^d$ independently of one another denotes $C_{1-6}$alkyl, $C_{4-11}$cycloalkylalkyl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl.

(B) Aspects relating to $R^2$ and $R^{2'}$ (B1) One aspect of the invention relates to compounds of general formula (1) or (1A), wherein $R^2$ and $R^{2'}$ each independently of one another denote $C_{1-6}$alkyl.

(B2) Another aspect of the invention relates to compounds of general formula (1) or (1A), wherein $R^2$ and $R^{2'}$ in each case independently of one another represent methyl or ethyl.

(B3) Another aspect of the invention relates to compounds of general formula (1) or (1A), wherein $R^2$ denotes $C_{3-8}$cycloalkyl.

(B4) Another aspect of the invention relates to compounds of general formula (1) or (1A), wherein $R^2$ denotes cyclopropyl.

(B5) One aspect of the invention relates to compounds of general formula (1) or (1A), wherein $R^2$ with $R^{2'}$ together with the enclosed nitrogen atom forms a 3-8 membered heterocycloalkyl, which may optionally contain one or more further hetero atoms, selected from among N, O and S.

(B6) Another aspect of the invention relates to compounds of general formula (1) or (1A), wherein $R^2$ with $R^{2'}$ together with the enclosed nitrogen atom forms azetidine, pyrrolidine or piperidine.

(B7) Another aspect of the invention relates to compounds of general formula (1) or (1A), wherein $R^2$ with $R^{2'}$ together with the enclosed nitrogen atom forms thiazolidine, thiomorpholine, morpholine or piperazine.

(C) Aspects relating to $R^4$ (C1) One aspect of the invention relates to compounds of general formula (1) or (1A), wherein $R^4$ denotes hydrogen.

(C2) Another aspect of the invention relates to compounds of general formula (1) or (1A), wherein $R^4$ denotes fluorine or chlorine.

(D) Aspects relating to $R^5$ (D1) One aspect of the invention relates to compounds of general formula (1) or (1A), wherein $R^5$ denotes hydrogen.

(D2) Another aspect of the invention relates to compounds of general formula (1) or (1A), wherein two $R^5$ form cyclopropyl.

All of the above-mentioned aspects (A1) to (A4) for $R^1$, (B1) to (B10) for $R^2$ and $R^{2'}$ (C1) and (C2) for $R^4$ and (D1) to (D4) for $R^5$ may be combined with one another as desired.

The Table below shows preferred combinations of various aspects of the compounds of formula (1) according to the invention:

| embodiment | $R^1$ | $R^2$ and $R^{2'}$ | $R^4$ | $R^5$ |
|---|---|---|---|---|
| I-1 | A1 | B1 | C1 | D1 |
| I-2 | A1 | B2 | C1 | D1 |
| I-3 | A1 | B3 | C1 | D1 |
| I-4 | A1 | B4 | C1 | D1 |
| I-5 | A1 | B5 | C1 | D1 |
| I-6 | A1 | B6 | C1 | D1 |
| I-7 | A1 | B7 | C1 | D1 |
| I-8 | A1 | B8 | C1 | D1 |

-continued

| embodiment | R¹ | R² and R²' | R⁴ | R⁵ |
|---|---|---|---|---|
| I-9 | A1 | B9 | C1 | D1 |
| I-10 | A1 | B1 | C2 | D1 |
| I-11 | A1 | B2 | C2 | D1 |
| I-12 | A1 | B3 | C2 | D1 |
| I-13 | A1 | B4 | C2 | D1 |
| I-14 | A1 | B5 | C2 | D1 |
| I-15 | A1 | B6 | C2 | D1 |
| I-16 | A1 | B7 | C2 | D1 |
| I-17 | A1 | B1 | C2 | D2 |
| I-18 | A1 | B2 | C2 | D2 |
| I-19 | A1 | B3 | C2 | D2 |
| I-20 | A1 | B4 | C2 | D2 |
| I-21 | A1 | B5 | C2 | D2 |
| I-22 | A1 | B6 | C2 | D2 |
| I-23 | A1 | B7 | C2 | D2 |
| I-24 | A1 | Bl | C1 | D2 |
| I-25 | A1 | B2 | C1 | D2 |
| I-26 | A1 | B3 | C1 | D2 |
| I-27 | A1 | B4 | C1 | D2 |
| I-28 | A1 | B5 | C1 | D2 |
| I-29 | A1 | B6 | C1 | D2 |
| I-30 | A1 | B7 | C1 | D2 |
| I-31 | A2 | Bl | C1 | D1 |
| I-32 | A2 | B2 | C1 | D1 |
| I-33 | A2 | B3 | C1 | D1 |
| I-34 | A2 | B4 | C1 | D1 |
| I-35 | A2 | B5 | C1 | D1 |
| I-36 | A2 | B6 | C1 | D1 |
| I-37 | A2 | B7 | C1 | D1 |
| I-38 | A2 | B8 | C1 | D1 |
| I-39 | A2 | B9 | C1 | D1 |
| I-40 | A2 | B1 | C2 | D1 |
| I-41 | A2 | B2 | C2 | D1 |
| I-42 | A2 | B3 | C2 | D1 |
| I-43 | A2 | B4 | C2 | D1 |
| I-44 | A2 | B5 | C2 | D1 |
| I-45 | A2 | B6 | C2 | D1 |
| I-46 | A2 | B7 | C2 | D1 |
| I-47 | A2 | B1 | C2 | D2 |
| I-48 | A2 | B2 | C2 | D2 |
| I-49 | A2 | B3 | C2 | D2 |
| I-50 | A2 | B4 | C2 | D2 |
| I-51 | A2 | B5 | C2 | D2 |
| I-52 | A2 | B6 | C2 | D2 |
| I-53 | A2 | B7 | C2 | D2 |
| I-54 | A2 | B1 | C1 | D2 |
| I-55 | A2 | B2 | C1 | D2 |
| I-56 | A2 | B3 | C1 | D2 |
| I-57 | A2 | B4 | C1 | D2 |
| I-58 | A2 | B5 | C1 | D2 |
| I-59 | A2 | B6 | C1 | D2 |
| I-60 | A2 | B7 | C1 | D2 |
| I-61 | A3 | B3 | C1 | D1 |
| I-62 | A3 | B4 | C1 | D1 |
| I-63 | A3 | B5 | C1 | D1 |
| I-64 | A3 | B6 | C1 | D1 |
| I-65 | A3 | B7 | C1 | D1 |
| I-66 | A3 | B8 | C1 | D1 |
| I-67 | A3 | B9 | C1 | D1 |
| I-68 | A3 | B1 | C2 | D1 |
| I-69 | A3 | B2 | C2 | D1 |
| I-70 | A3 | B3 | C2 | D1 |
| I-71 | A3 | B4 | C2 | D1 |
| I-72 | A3 | B5 | C2 | D1 |
| I-73 | A3 | B6 | C2 | D1 |
| I-74 | A3 | B/ | C2 | D1 |
| I-75 | A3 | B1 | C2 | D2 |
| I-76 | A3 | B2 | C2 | D2 |
| I-77 | A3 | B3 | C2 | D2 |
| I-78 | A3 | B4 | C2 | D2 |
| I-79 | A3 | B5 | C2 | D2 |
| I-80 | A3 | B6 | C2 | D2 |
| I-81 | A3 | B7 | C2 | D2 |
| I-82 | A3 | B1 | C1 | D2 |
| I-83 | A3 | B2 | C1 | D2 |
| I-84 | A3 | B3 | C1 | D2 |
| I-85 | A3 | B4 | C1 | D2 |

-continued

| embodiment | R¹ | R² and R²' | R⁴ | R⁵ |
|---|---|---|---|---|
| I-86 | A3 | B5 | C1 | D2 |
| I-87 | A3 | B6 | C1 | D2 |
| I-88 | A3 | B7 | C1 | D2 |

One aspect of the invention relates to compounds of general formula (1) or (1A), or the pharmacologically effective salts thereof, as medicaments.

One aspect of the invention relates to compounds of general formula (1) or (1A), or the pharmacologically effective salts thereof, for preparing a medicament with an antiproliferative activity.

One aspect of the invention is a pharmaceutical preparation, containing as active substance one or more compounds of general formula (1) or (1A), according to one of claims 1 to 5 or the pharmacologically effective salts thereof optionally in combination with conventional excipients and/or carriers.

One aspect of the invention is the use of compounds of general formula (1) or (1A), for preparing a medicament for the treatment and/or prevention of cancer.

One aspect of the invention is a pharmaceutical preparation comprising a compound of general formula (1) or (1A) and at least one other cytostatic or cytotoxic active substance different from formula (1) or (1A), optionally in the form of the tautomers, the racemates, the enantiomers, the diastereomers and the mixtures thereof, as well as optionally the pharmacologically acceptable salts thereof.

DEFINITIONS

As used herein the following definitions apply, unless stated otherwise.

By alkyl substituents are meant in each case saturated, unsaturated, straight-chain or branched aliphatic hydrocarbon groups (alkyl group) and this includes both saturated alkyl groups and unsaturated alkenyl and alkynyl groups. Alkenyl substituents are in each case straight-chain or branched, unsaturated alkyl groups, which have at least one double bond. By alkynyl substituents are meant in each case straight-chain or branched, unsaturated alkyl groups, which have at least one triple bond.

The term heteroalkyl refers to groups which can be derived from alkyl as defined above in its broadest sense by replacing one or more of the groups —CH₃ in the hydrocarbon chains independently of one another by the groups —OH, —SH or —NH₂, one or more of the groups —CH₂— independently of one another by the groups —O—, —S— or —NH—, one or more of the groups

by the group

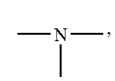

one or more of the groups =CH— by the group =N—, one or more of the groups =CH₂ by the group =NH or one or more of the groups =CH by the group =N, while in all only a maximum of three heteroatoms may be present in a heteroalkyl, there must be at least one carbon atom between two oxygen and between two sulphur atoms or between one oxygen and one sulphur atom and the group as a whole must have chemical stability.

It flows from the indirect definition/derivation from alkyl that heteroalkyl is made up of the sub-groups of saturated hydrocarbon chains with hetero-atom(s), heteroalkenyl and heteroalkynyl, while further subdivision into straight-chain (unbranched) and branched may be carried out. If a heteroalkyl is supposed to be substituted, the substitution may take place independently of one another, in each case monoor polysubstituted, at all the hydrogen-carrying oxygen, sulphur, nitrogen and/or carbon atoms. Heteroalkyl itself may be linked to the molecule as substituent both through a carbon atom and through a heteroatom.

By way of example, the following representative compounds are listed: dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-diisopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxyethyl; 3-hydroxypropyl; methoxy; ethoxy; propoxy; methoxymethyl; 2-methoxyethyl etc.

Haloalkyl relates to alkyl groups, wherein one or more hydrogen atoms are replaced by halogen atoms. Haloalkyl includes both saturated alkyl groups and unsaturated alkenyl and alkynyl groups, such as for example —CF₃, —CHF₂, —CH₂F, —CF₂CF₃, —CHFCF₃, —CH₂CF₃, —CF₂CH₃, —CHFCH₃, —CF₂CF₂CF₃, —CF₂CH₂CH₃, —CF=CF₂, —CCl=CH₂, —CBr=CH₂, —CI=CH₂, —C≡C—CF₃, —CHFCH₂CH₃ and —CHFCH₂CF₃.

Halogen refers to fluorine, chlorine, bromine and/or iodine atoms.

By cycloalkyl is meant a mono or bicyclic ring, while the ring system may be a saturated ring or, however, an unsaturated, non-aromatic ring, which may optionally also contain double bonds, such as for example cyclopropyl, cyclopropenyl, cyclobutyl, cyclobutenyl, cyclopentyl, cyclopentenyl, cyclohexyl, cyclohexenyl, norbornyl and norbornenyl.

Cycloalkylalkyl includes a non-cyclic alkyl group wherein a hydrogen atom bound to a carbon atom, usually to a terminal C atom, is replaced by a cycloalkyl group.

Aryl relates to monocyclic or bicyclic aromatic rings with 6-10 carbon atoms such as phenyl and naphthyl, for example.

Arylalkyl includes a non-cyclic alkyl group wherein a hydrogen atom bound to a carbon atom, usually to a terminal C atom, is replaced by an aryl group.

By heteroaryl are meant mono- or bicyclic aromatic rings, which instead of one or more carbon atoms contain one or more, identical or different hetero atoms, such as e.g. nitrogen, sulphur or oxygen atoms. Examples include furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl. Examples of bicyclic heteroaryl groups are indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl and benzotriazinyl, indolizinyl, oxazolopyridyl, imidazopyridyl, naphthyridinyl, indolinyl, isochromanyl, chromanyl, tetrahydroisoquinolinyl, isoindolinyl, isobenzotetrahydrofuryl, isobenzotetrahydrothienyl, isobenzothienyl, benzoxazolyl, pyridopyridyl, benzotetrahydrofuryl, benzotetrahydrothienyl, purinyl, benzodioxolyl, triazinyl, phenoxazinyl, phenothiazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridyl-N-oxide tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyridazinyl-N-oxide, pyrazinyl-N-oxide, quinolinyl-N-oxide, indolyl-N-oxide, indolinyl-N-oxide, isoquinolyl-N-oxide, quinazolinyl-N-oxide, quinoxalinyl-N-oxide, phthalazinyl-N-oxide, imidazolyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, tetrazolyl-N-oxide, benzothiopyranyl-S-oxide and benzothiopyranyl-S,S-dioxide.

Heteroarylalkyl encompasses a non-cyclic alkyl group wherein a hydrogen atom bound to a carbon atom, usually to a terminal C atom, is replaced by a heteroaryl group.

Heterocycloalkyl relates to saturated or unsaturated, non-aromatic mono-, bicyclic or bridged bicyclic rings comprising 3-12 carbon atoms, which instead of one or more carbon atoms carry heteroatoms, such as nitrogen, oxygen or sulphur. Examples of such heterocyloalkyl groups are tetrahydrofuryl, pyrrolidinyl, pyrrolinyl, imidazolidinyl, imidazolinyl, pyrazolidinyl, pyrazolinyl, piperidinyl, piperazinyl, indolinyl, isoindolinyl, morpholinyl, thiomorpholinyl, homomorpholinyl, homopiperidinyl, homopiperazinyl, homothiomorpholinyl, thiomorpholinyl-S-oxide, thiomorpholinyl-S,S-dioxide, tetrahydropyranyl, tetrahydrothienyl, homothiomorpholinyl-S,S-dioxide, oxazolidinonyl, dihydropyrazolyl, dihydropyrrolyl, dihydropyrazinyl, dihydropyridyl, dihydropyrimidinyl, dihydrofuryl, dihydropyranyl, tetrahydrothienyl-S-oxide, tetrahydrothienyl-S,S-dioxide, homothiomorpholinyl-S-oxide, 2-oxa-5-azabicyclo[2,2,1]heptane, 8-oxa-3-aza-bicyclo [3.2.1]octane, 3.8-diaza-bicyclo[3.2.1]octane, 2,5-diaza-bicyclo[2,2,1]heptane, 3.8-diaza-bicyclo[3.2.1]octane, 3.9-diaza-bicyclo[4.2.1]nonane and 2.6-diaza-bicyclo[3.2.2] nonane.

Heterocycloalkylalkyl relates to a non-cyclic alkyl group wherein a hydrogen atom bound to a carbon atom, usually to a terminal C atom, is replaced by a heterocycloalkyl group.

The following Examples illustrate the present invention without restricting its scope.

Analytical Methods

| Method AM1: | |
|---|---|
| HPLC: | Agilent 1100 Series; MS: 1100 Series LC/MSD (API-ES (+/−3000 V, Quadrupole, G1946D); Mode: Scan pos 100-1000, neg 100-1000 |
| column: | Waters; Part No. 186000594; XTerra MS C18 2.5 µm; 2.1 × 50 mm column |

-continued

| Method AM1: | |
|---|---|
| solvent: | A: H₂O desalinated with the addition of 0.1% formic acid<br>B: acetonitrile HPLC grade with the addition of 0.1% formic acid |
| detection: | peakwide >0.1 mm (2 s); 190-450 nm<br>UV 254 nm (bandwide 8, reference off)<br>UV 230 nm (bandwide 8, reference off) |
| injection: | 1 µL standard injection |
| flow: | 0.6 mL/min |
| column temperature: | 35° C. |
| pump gradient: | 0.0-0.5 min    5% B<br>0.5-1.5 min    5% -> 50% B<br>1.5-4.0 min    50% -> 95% B<br>4.0-6.0 min    95% B<br>6.0-6.5 min    95% -> 5% B<br>1.5 min post run    5% B |

| Method AM2 | |
|---|---|
| HPLC: | Agilent Series 1100 (G1379A/G1310A converted to G1311A/G1313A/G1316A/G1948D/G1315B/G1946D) Mode: Scan pos 100-1000, neg 100-1000 |
| column: | Agilent Zorbax SB-C8, 2.1 × 50 mm, 3.5 µm |
| solvent: | A: H₂O desalinated with the addition of 0.1% formic acid<br>B: acetonitrile HPLC grade with the addition of 0.1% formic acid |
| detection: | peakwide >0.1 min (2 s); 190-450 nm<br>UV 254 nm (bandwide 8, reference off)<br>UV 230 nm (bandwide 8, reference off) |
| injection: | 2.5 µL standard injection |
| flow: | 0.6 mL/min |
| column temperature: | 35 C. ° |
| pump gradient: | 0-3.0 min    10% -> 90% B<br>3.0-4.0 min    90% B<br>4.0-5.0 min    90% -> 10% B |

| Method AM3 | |
|---|---|
| HPLC: | Agilent Series 1100 (G1312A/G1315A/G1316A/G1367A) Agilent MSD SL ESI |
| Mode: | Scan pos 150-750 |
| column: | Agilent Zorbax SB-C8, 2.1 × 50 mm, 3.5 µm |
| solvent: | A: H₂O desalinated with the addition of 0.1% formic acid<br>B: acetonitrile HPLC grade with the addition of 0.1% formic acid |
| detection: | peakwidth >0.01 min (0.2 s); 190-450 nm<br>UV 254 nm (bandwide 16, reference off)<br>UV 230 nm (bandwide 8, reference off)<br>UV 214 nm (bandwide 8, reference off) |
| injection: | 3.0 µL overlap injection |
| flow: | 1.1 mL/min |
| column temperature: | 45° C. |
| pump gradient: | 0-1.75 min    15% -> 95% B<br>1.75-1.90 min    95% B<br>1.90-1.92 min    950% -> 15% B |

| Method AM4 | | |
|---|---|---|
| HPLC: | Agilent 1100 Series | |
| MS: | Agilent LC/MSD SL | (LCMS 1: 1100 series LC/MSD) |
| column: | Waters, Xterra MS C18, 2.5 µm, 2.1 × 30 mm, Part. No. 186000592 | |
| solvent | A: H₂O desalinated with the addition of 0.1% formic acid<br>B: acetonitrile HPLC grade with the addition of 0.1% formic acid | |
| detection: | MS:    Positive and negative | |
| | Mass range:    120-900 m/z | |
| | Fragmentor:    120 | |
| | Gain EMV:    1 | |
| | Threshold:    150 | |
| | Stepsize:    0.25 | |
| | UV:    254 nm | |
| | Bandwide:    1 | (LCMS1: 2) |
| | Reference:    off | |
| | Spectrum: | |
| | Range:    250-400 nm | |
| | Range step:    1.00 nm | |
| | Threshold:    4.00 nAU | |
| | Peakwidth:    <0.01 min | (LCMS1: >0.05 min) |
| | Slit:    1 nm | (LCMS1: 2 nm) |
| injection: | 5 µL | |
| flow: | 1.10 mL/min | |
| column temperature: | 40° C. | |
| gradient: | 0.00 min    5% B | |
| | 0.00-2.50 min    5% -> 95% B | |
| | 2.50-2.80 min    95% B | |
| | 2.81-3.10 min    95% -> 5% B | |

| Method AM5 | | |
|---|---|---|
| HPLC: | Agilent 1100 Series | |
| MS: | Agilent LC/MSD SL | (LCMS 1: 1100 series LC/MSD) |
| Column: | Phenomenex, Synergi Polar RP 80A, 4 µm, 2 × 30 mm, Part. No. 00A-4336-B0 | |
| Solvent: | A: H$_2$O (Millipore purified purest water) with the addition of 0.1% formic acid | |
| | B: acetonitrile (HPLC grade) | |
| Detection: | MS: Positive and negative | |
| | Mass range: 120-900 m/z | |
| | Fragmentor: 120 | |
| Gain EMV: | 1 | |
| Threshold: | 150 | |
| Stepsize: | 0.25 | |
| UV: | 254 nm | |
| Bandwide: | 1 | (LCMS1: 2) |
| Reference: | off | |
| Spectrum: | | |
| | Range: 250-400 nm | |
| | Range step: 1.00 nm | |
| | Threshold: 4.00 mAU | |
| | Peakwidth: <0.01 min | (LCMS1: >0.05 min) |
| | Slit: 1 nm | (LCMS1: 2 nm) |
| Injection: | Inj. Vol.: 5 µL | |
| Inj. mode: | Needle wash | |
| Separation: | Flow: 1.10 mL/min | |
| | Column temp.: 40° C. | |
| | gradient: 0.00 min | 5% solvent B |
| | 0.00-2.50 min | 5% -> 95% solvent B |
| | 2.50-2.80 min | 95% solvent B |
| | 2.81-3.10 min | 95% -> 5% solvent B |

| Method AM6 | |
|---|---|
| HPLC: | Waters Alliance 2695 |
| column: | Waters, Xterra MS C18, 2.5 µm, 4.6 × 30 mm, Part. No. 186000600 |
| solvent | A: H$_2$O desalinated with the addition of 0.1% formic acid |
| | B: acetonitrile HPLC grade with the addition of 0.08% formic acid |
| flow: | 1 mL/min |
| column temperature: | 25° C. |
| gradient: | 0.00 min 5% B |
| | 0.00-3.10 min 5% -> 98% B |
| | 3.10-4.50 min 98% B |
| | 4.50-5.00 min 98% -> 5% B |

| Abbreviations used | |
|---|---|
| d | day |
| DC | thin layer chromatography |
| DMF | N,N-dimethylformamide |
| DMSO | dimethylsulphoxide |
| h | hour |
| HPLC | high performance liquid chromatography |
| M | molar |
| min | minute |
| mL | milliliter |
| MS | mass spectrometry |
| N | normal |
| NMR | nuclear resonance spectroscopy |
| ppm | part per million |
| Rf | retention factor |
| RP | reversed phase |
| RT | ambient temperature |
| Rt | retention time |
| m.p | melting point |

| -continued | |
|---|---|
| Abbreviations used | |
| tert | tertiary |
| THF | tetrahydrofuran |

Synthesis of the Reagents

H-1) (2-chloro-4-morpholin-4-ylmethyl-phenyl)-hydrazine dihydrochloride

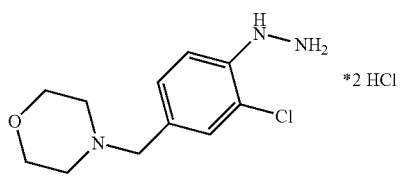

H-1a) 4-bromo-3-chlorobenzyl bromide

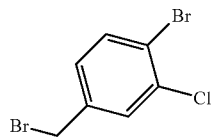

A suspension of N-bromosuccinimide (16.4 g, 87.4 mmol), 4-bromo-chlorotoluene (18.2 g, 87.4 mmol) and α,α'- azoisobutyronitrile (0.67 g, 4 mmol) in 90 mL dichloromethane is heated in the microwave for 1 min at 100° C. and then cooled overnight at −20° C. The resulting white precipitate is filtered and the filtrate is evaporated down. The residue is stirred with 100 mL diethyl ether, filtered, evaporated down and filtered again.

Yield: 24.1 g

H-1b) 1-bromo-2-chloro-4-morpholin-4-ylmethyl-benzene

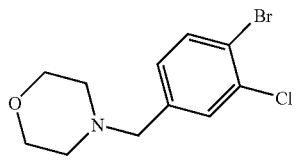

At 0° C. a solution of H-1a (24.1 g, 84.7 mmol) is very slowly added dropwise to a solution of morpholine (23.1 mL, 262 mmol) in 250 mL tetrahydrofuran. The reaction mixture is stirred overnight at RT, filtered and evaporated down. The residue is combined successively with 250 mL dichloromethane, 100 mL water and then with 200 mL 1 M aqueous hydrochloric acid. After cooling in the ice bath the precipitate formed is filtered and washed twice with ice water and then with dichloromethane.

Yield: 12.9 g

Then this intermediate compound is combined with 100 mL water and adjusted to pH 9 with aqueous potassium carbonate solution. The aqueous phase is extracted three times with 150 mL ethyl acetate. The combined organic phases are dried on magnesium sulphate, filtered and evaporated down. Yield 11.2 g H-1c) N-(2-chloro-4-morpholin-4-ylmethyl-phenyl)-benzophenone-hydrazone

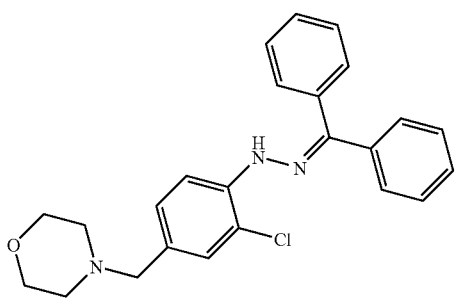

Under an argon atmosphere a solution of H-1b (11.2 g, 38.5 mmol) in 500 mL toluene is added to a mixture of benzophenonehydrazone (7.72 g, 38.5 mmol), sodium-tert-butoxide (5.73 g, 57.8 mmol), palladium(II)acetate (0.13 g, 0.58 mmol) and rac-BINAP (0.49 g, 0.77 mmol). The reaction mixture is refluxed for 3 h with stirring and then mixed with 10 g Celite, filtered through a Celite bed and evaporated down. The residue is combined with 50 mL 1-propanol and left to stand overnight. The precipitate formed is filtered. Yield: 10.9 g. 30 mL 1-propanol and 30 mL 37% hydrochloric acid are added to H-1c (10.8 g, 26.6 mmol) and the reaction mixture is heated for 1.5 min at 130° C. in the microwave. The desired product crystallises out after some time. Yield: 6.69 g.

H-2) (4-[1-N,N-dimethylamino-cyclopropyl-1-yl]-phenyl)-hydrazine dihydrochloride

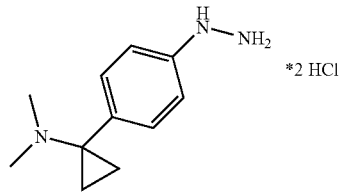

H-2a) 1-(4-bromophenyl)-1-cyclopropylcarboxylic acid

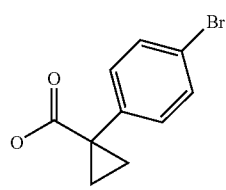

At 5° C. bromine (1.5 mL, 30 mmol) is added dropwise to a solution of 1-phenyl-1-cyclopropylcarboxylic acid (5 g, 30 mmol) and sodiumacetate (2.7 g, 33 mmol) in 30 mL glacial acetic acid. Then the mixture is heated to 50° C. and stirred for 2 days. The reaction mixture is diluted with 100 mL water, and the precipitate formed is filtered off and washed with 50% acetic acid. Yield: 5.7 g.

H-2b) tert-butyl 1-(4-bromophenyl)-1-cyclopropylcarbamidate

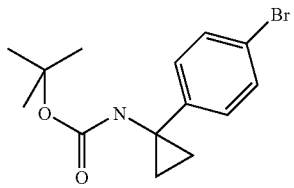

Under an argon atmosphere a suspension of H-2a (5.7 g, 24 mmol), N-ethyldiisopropylamine (5.3 mL, 31 mmol), tert-butanol (55 mL, 0.59 mol), diphenylphosphorylazide (6.1 mL, 28 mmol) and activated molecular sieve (4 Å) in 120 mL toluene is refluxed for 5 h. The reaction mixture is evaporated down and the residue is combined with 100 mL ethyl acetate and extracted with 50 mL of 5% citric acid solution, saturated sodium hydrogen carbonate solution and saturated sodium chloride solution. The organic phase is dried on magnesium sulphate and evaporated down. Yield 7.7 g.

H-2c) tert-butyl N-methyl-1-(4-bromophenyl)-1-cyclopropylcarbamidate-

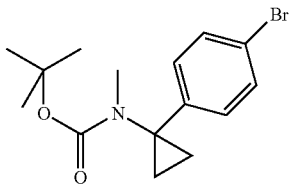

Sodium hydride (60% in mineral oil, 6.2 g, 0.15 mol) is added at RT to a solution of H-2b (32 g, 0.1 mol) in 300 mL DMF. After 10 min the mixture is heated to 40° and 15 min later methyl iodide (14 mL, 0.23 mol) is added and the mixture is stirred for another 1 h at 40° C. The reaction mixture is added to 1.2 L ice water, stirred for 15 min and then extracted three times with 500 mL ethyl acetate. The combined organic phases are dried on magnesium sulphate and evaporated down. Yield: 38 g (w=0.85)

H-2d) N-methyl-1-(4-bromophenyl)-1-cyclopropylamine hydrochloride

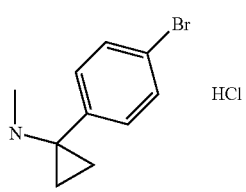

A solution of H-2c (34 g, 0.1 mol) in 260 mL hydrochloric acid (4 M in dioxane) is stirred for 1 h at RT and then evaporated down. Yield: 31 g (w=0.85)

H-2e) N,N-dimethyl-1-(4-bromophenyl)-1-cyclopropylamine hydrochloride

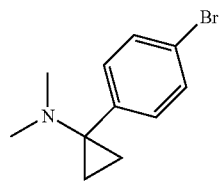

35% formaldehyde in water (40 mL, 0.5 mol) is slowly added to a solution of H-2d (30 g, 0.1 mol) in 400 mL dichloroethane/methanol (1:1) and stirred vigorously for 30 min at RT. Then glacial acetic acid (8.6 mL, 0.15 mol) and sodium trisacetoxy-borohydride (32 g, 0.15 mol) are added batchwise and the mixture is stirred overnight at RT. The reaction mixture is combined with 500 mL saturated sodium hydrogen carbonate solution and stirred for 30 min. The phases are separated and the aqueous phase is extracted with 500 mL dichloromethane. The combined organic phases are dried and evaporated down, and the residue is purified by chromatography on silica gel with cyclohexane/ethyl acetate. Yield: 10.2 g.

H-2f) N-([1-N,N-dimethylamino-1 cyclopropyl-1-yl]-phenyl)-benzophenonehydrazone

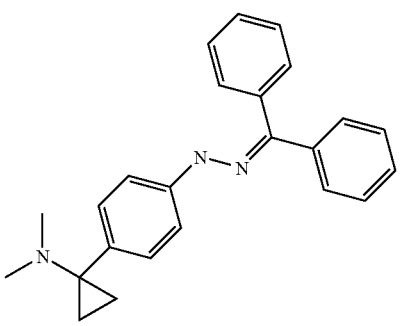

Analogously to the preparation of H-1c the desired compound is obtained starting from H-2e (10 g, 42 mmol), benzophenonehydrazone (8.3 g, 42 mmol), sodium-tert-butoxide (6.1 g, 64 mmol), palladium(II)acetate (0.19 g, 0.85 mmol) and rac-BINAP (1.1 g, 1.7 mmol).

Yield: 9.1 g.

A solution of H-2f (8.9 g, 25 mmol) in 30 mL 1-propanol and 31 mL 37% hydrochloric acid is refluxed for 1 h with stirring. The reaction mixture is evaporated down, taken up again in 1-propanol and evaporated down again. The residue is stirred overnight in 150 mL acetonitrile, and the precipitate formed is filtered off. Yield: 4.3 g.

H-3) [4-(1-pyrrolidin-1-yl-cyclopropyl)-phenyl]-hydrazine-bis-trifluoroacetate

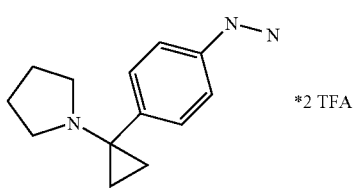

H-3a) 1-(4-bromophenyl)-1-cyclopropylamine hydrochloride

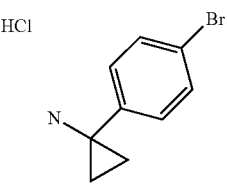

47 mL hydrochloric acid (4 M in dioxane) is added to a solution of H-2b (19.5 g, 37.4 mmol) in 50 mL dioxane and stirred overnight at RT. The precipitate formed is filtered off, the filtrate is evaporated down to about half and filtered again. The filter cakes are combined and dried. Yield: 10.1 g (w=0.90)

H-3b) 4-bromo-(1-pyrrolidin-1-yl-cyclopropyl-1-yl)-benzene

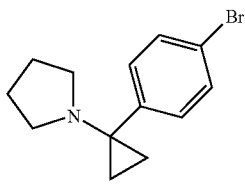

1,4-Dibromobutane (0.19 mL, 1.7 mmol) is added to a suspension of H-3a (0.5 g, 1.7 mmol), potassium carbonate (0.73 g, 5.2 mmol) and potassium iodide (3 mg, 0.02 mmol) in 10 mL acetonitrile and then refluxed for 24 h. The reaction mixture is filtered off, evaporated down and the residue is purified by RP-HPLC chromatography. Yield: 0.19 g.

H-3c) di-tert-butyl N,N'-[4-(1-pyrrolidin-1-yl-cyclopropyl)-phenyl]-hydrazinedicarboxylate

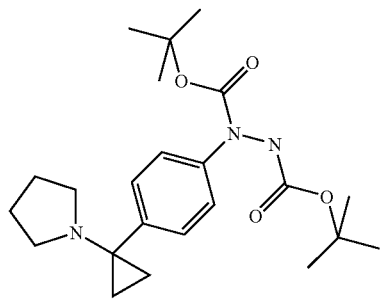

A solution of H-3b (0.19 g, 0.7 mmol) in 3 mL dry THF is added at −78° C. under an argon atmosphere to a solution of n-butyllithium (0.84 mL, 2.5 M in hexane) in 5 mL dry THF. Then a solution of di-tert-butyl-azodicarboxylate (0.19 g, 0.84 mmol) in 4 mL dry THF is added. After 5 min the cooling bath is removed and after another 20 min the reaction mixture is combined with 10 mL water and 20 mL ethyl acetate. The phases are separated and the aqueous phase is extracted with 10 mL ethyl acetate. The combined organic phases are dried on magnesium sulphate and evaporated down. Yield: 0.31 g (w=0.9) Trifluoroacetic acid (0.1 mL, 2 mmol) is added to a solution of H-3c (0.29 g, 0.7 mmol) in 4 mL dichloromethane and the mixture is stirred for 1 h at RT. Then the reaction mixture is evaporated down. Yield: 0.33 g (w=0.9)

H-4) (4-[1-morpholin-1-yl-cyclopropyl-1-yl]-phenyl)-hydrazine-bis-trifluoroacetate

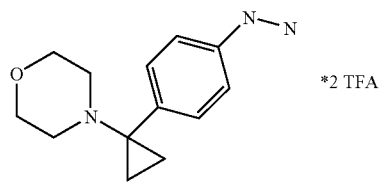

H-4-a) 4-bromo-(1-morpholin-1-yl-cyclopropyl-1-yl)-benzene

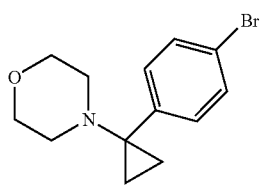

The desired compound is obtained analogously to the preparation of H-3b starting from H-3a (0.5 g, 1.7 mmol), potassium carbonate (0.73 g, 5.2 mmol), potassium iodide (3 mg, 0.02 mmol) and bis(2-bromethyl)ether. Yield: 0.32 g.

H-4-b) di-tert-butyl N,N'-[4-(1-morpholin-4-yl-cyclopropyl)-phenyl]-hydrazinedicarboxylate

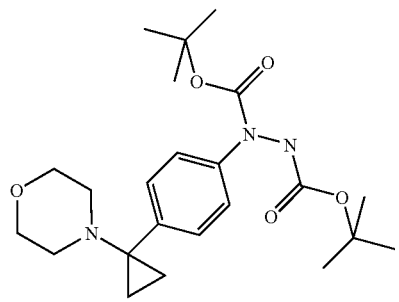

The desired compound is obtained analogously to the preparation of H-3c starting from H-4a (0.22 g, 0.76 mmol), n-butyllithium (0.92 mL, 2.5 M in hexane) and di-tert-butylazodicarboxylate (0.21 g, 0.92 mmol). Yield: 0.34 g.

The desired compound is obtained analogously to the preparation of H-3 starting from H-4b (0.29 g, 0.7 mmol) and trifluoroacetic acid (0.1 mL, 2 mmol). Yield: 0.36 g (w=0.9)

H-5) (4-imidazol-1-ylmethyl-phenyl)-hydrazine

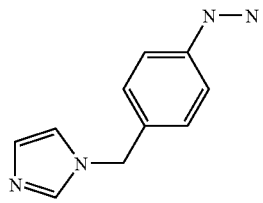

H-5a) 1-(4-nitro-benzyl)-1H-imidazole

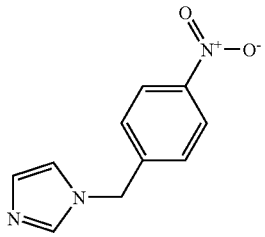

Potassium carbonate (3.1 g, 23 mmol) is added to a solution of 4-nitrobenzylbromide (5 g, 23 mmol) and imidazole (1.6 g, 23 mmol) and the reaction mixture is stirred at RT. After the reaction has been completed according to HPLC-MS the suspension is poured into 800 mL water and extracted three times with ethyl acetate. The combined organic phases are washed with saturated sodium chloride solution, dried on sodium sulphate and evaporated down. The residue is purified by chromatography on silica gel with dichloromethane/methanol. Yield: 2.1 g.

H-5b) 4-imidazol-1-ylmethyl-phenylamine

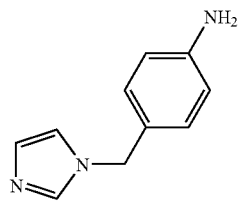

A solution of H-5a (2.1 g, 10 mmol) in 10 mL ethanol, 10 mL ethyl acetate and 13 mL 1 M hydrochloric acid is combined with palladium (10% on activated charcoal, 0.27 g) in a hydrogenation reactor and stirred overnight at RT under 3.4 bar hydrogen pressure. The reaction mixture is filtered, evaporated down and codistilled three times with ethanol.

Yield: 1.8 g.

A solution of sodium nitrite (0.77 g, 10 mmol) in 5 mL water is added at −10° C. to a solution of H-5b (1.8 g, 10 mmol) in 10 mL 37% hydrochloric acid. After 20 min stirring at 0° C. a solution of tin(II)chloride dihydrate (8.9 g, 39 mmol) in 10 mL 37% hydrochloric acid is again added at −10° C. The reaction mixture is heated to RT, made basic with 10 N sodium hydroxide solution and extracted with ethyl acetate. The aqueous phase is filtered and extracted with dichloromethane. The combined organic phases are dried and evaporated down. Yield: 0.32 g.

H-6) 2-fluoro-4-hydrazino-benzonitrile hydrochloride

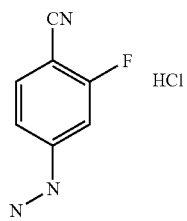

H-6a) 4-amino-2-fluoro-benzonitrile

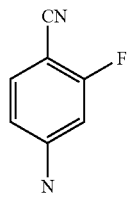

A solution of 2-fluoro-4-nitrobenzonitrile (5 g, 30 mmol) in 300 mL methanol is stirred in a hydrogenation reactor with palladium (5% on activated charcoal, 400 mg) for 2 h at RT and 2 bar hydrogen pressure. The reaction mixture is filtered and evaporated down.

Yield: 4 g.

The desired compound is obtained as the hydrochloride analogously to the preparation of H-5, starting from H-6a (4 g, 29 mmol), sodium nitrite (3.2 g, 46 mmol) and tin(II) chloride dihydrate (26 g, 0.12 mol), after the addition of 10 mL of a 2 M solution of HCl in dioxane. Yield: 4.3 g (w=0.7)

H-7) 4-fluoro-3-hydrazino-benzonitrile

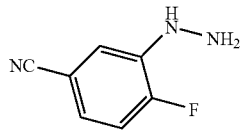

4-fluoro-3-nitrobenzonitrile (5 g, 30 mmol) is first of all subjected to catalytic hydrogenation with 5% palladium on activated charcoal (0.4 g) in 300 mL methanol (2 h at 2 bar hydrogen pressure), whereupon the 3-amino-4-fluorobenzonitrile formed is obtained as a solid after filtration and evaporation of the solvent. Yield: 4.1 g.

The desired product H-7 is obtained analogously to the preparation of H-5 starting from 3-amino-4-fluorobenzonitrile (4.1 g, 30 mmol), sodium nitrite (3.1 g, 45 mmol), tin(II) chloride dihydrate (27 g, 119 mmol) in a total of 130 mL hydrochloric acid (w=0.32) and 40 mL water. Yield: 4.1 g Z-1) N-[7-oxo-6-(pyridin-3-carbonyl)-4,5,6,7-tetrahydro-benzothiazol-2-yl]-acetamide

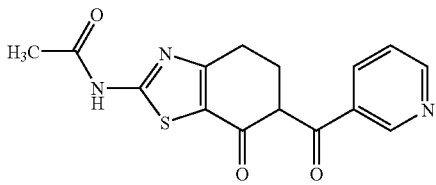

The synthesis of Z-1 is described in DE102004048877.

Z-2) methyl [7-oxo-6-(pyridin-3-carbonyl)-4,5,6,7-tetrahydro-benzothiazole-2-yl]-carbamidate

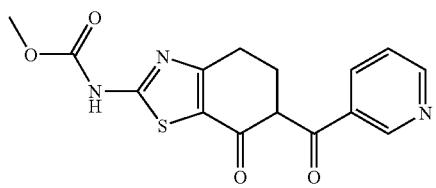

Z-2a) methyl [7-oxo-4,5,6,7-tetrahydro-benzothiazol-2-yl]-carbamidate

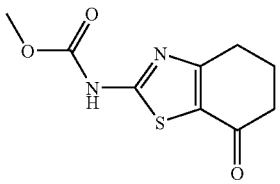

A solution of methylchloroformate (15 mL, 0.2 mol) in 15 mL trockenem THF is added to a suspension of 2-amino-5,6-dihydro-4-H-benzothiazol-7-one (30 g, 0.18 mol) in 500 mL dry THF and then refluxed overnight with stirring. The reaction mixture is filtered, the filtrate is evaporated down, and the solid residue is stirred with diethyl ether, filtered again and dried. Yield: 20 g.

200 mL LiHMDS (1M in THF) are added dropwise to a solution of Z-2a (15 g, 66 mmol) in 1.2 L dry THF at −10° C. under an argon atmosphere and the mixture is stirred for 4 h. Then a solution of 3-pyridylcarbonyl-N-imidazolide (23 g, 0.13 mol) in 85 mL dry THF is added to the suspension. After 1 h the cooling bath is removed and the reaction mixture is stirred overnight at RT. The solvent is decanted off and the residue is combined with dichloromethane and saturated sodium hydrogen carbonate solution. The phases are separated and the aqueous phase is extracted with dichloromethane. The combined organic phases are dried on magnesium sulphate, evaporated down, and the residue is stirred with 200 mL diethyl ether. The precipitate is filtered, treated with ultrasound in 200 mL acetonitrile for 1 h and filtered off. Yield: 9.3 g.

Z-3) N-[1-(2-chloro-4-formyl-phenyl)-3-pyridin-3-yl-4,5-dihydro-1H-pyrazolo[4,3-g]benzothiazol-7-yl]-acetamide

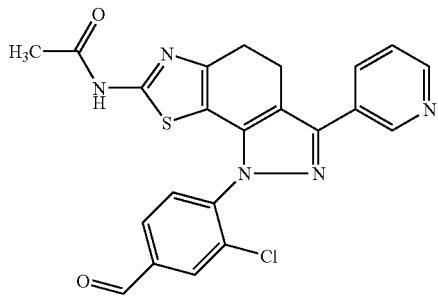

In a hydrogenation reactor under an argon atmosphere, triethylammonium hypophosphite hydrate (2.2 mL, 12 mmol) is added at 10° C. to a suspension of Raney nickel (8 g, 93 mmol) in 75 mL dichloromethane and 75 mL methanol. After the release of gas has died away N-[1-(2-chloro-4-cyanophenyl)-3-pyridin-3-yl-4,5-dihydro-1H-pyrazolo[4,3-g]benzothiazol-7-yl]-acetamide (PCT/EP05055021) (2.7 g, 5.6 mmol) is added and the mixture is stirred for 3 h at 55° C. The reaction mixture is filtered and the filtrate is evaporated down. The residue is purified on silica gel with dichloromethane/methanol.
Yield: 1.1 g.

Z-4) N-[1-(3-dimethylamino-4-formyl-phenyl)-3-pyridin-3-yl-4,5-dihydro-1H-pyrazolo[4,3-g]benzothiazol-7-yl]-acetamide

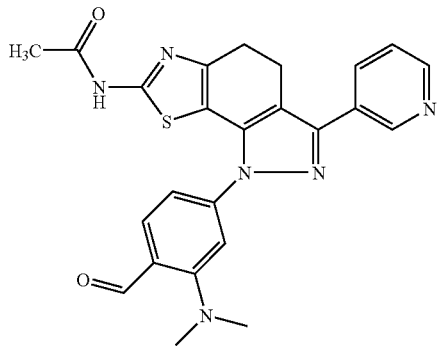

Z-4-a) N-[1-(3-chloro-4-cyanophenyl)-3-pyridin-3-yl-4,5-dihydro-1H-pyrazolo[4,3-g]benzothiazol-7-yl]-acetamide

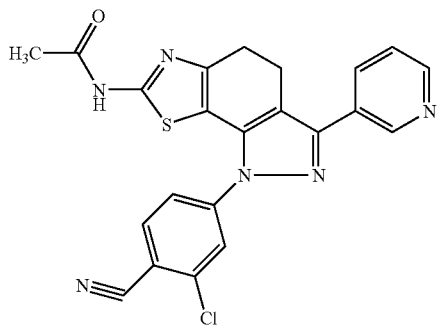

A solution of Z-1 (5.1 g, 16 mmol) and H-6 (4.3 g, 16 mmol) in 180 mL glacial acetic acid is stirred for 14 h at 50° C. The reaction mixture is evaporated down and then added to ice water. The precipitate formed is filtered. Yield: 5.2 g (w=0.9).

Z-4b) N-[1-(4-cyano-3-dimethylamino-phenyl)-3-pyridin-3-yl-4,5-dihydro-1H-pyrazolo[4,3-g]benzothiazol-7-yl]-acetamide

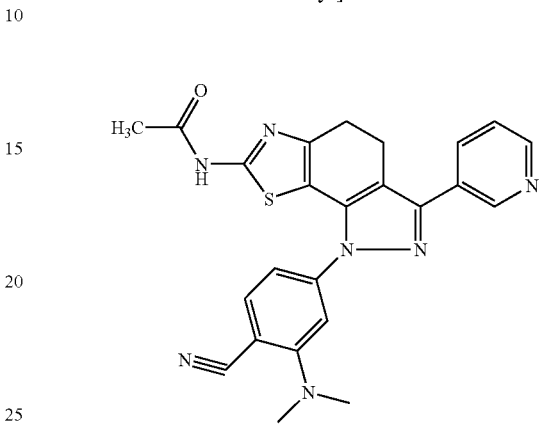

A solution of Z-4a (0.2 g, 0.33 mmol) and dimethylamine (0.81 mL, 1.6 mmol) in 2 mL DMSO is heated for 15 min at 130° C. in the microwave and then water is added. The precipitate formed is filtered off and purified by chromatography on silica gel with dichloromethane/methanol. Yield: 82 mg.

Raney nickel (0.2 g, 3.4 mmol) is added to a solution of Z-4b (100 mg, 0.22 mmol) in 1.5 mL pyridine and 0.7 mL glacial acetic acid and then the mixture is stirred for 2 h at 50° C. The reaction mixture is filtered through Celite and the filtrate is evaporated down. The residue is purified by RP-HPLC chromatography. Yield: 53 mg.

Z-5) 1-(2-chloro-4-dimethylaminomethylphenyl)-3-pyridin-3-yl-4,5-dihydro-1H-pyrazolo[4,3-g]benzothiazol-7-ylamine

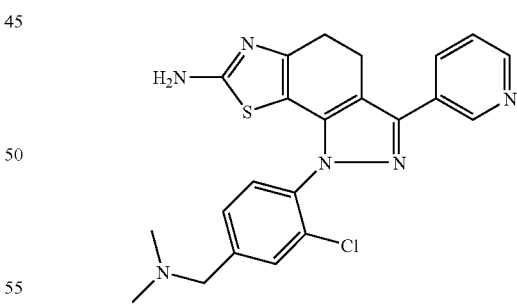

Under an argon atmosphere at −78° C. a solution of lithium aluminium hydride (1 M in THF, 3 mL) is added to a solution of 4-(7-amino-3-pyridin-3-yl-4,5-dihydro-pyrazolo[4,3-g]benzothiazol-1-yl)-3-chloro-N,N-dimethylbenzamide (PCT/EP05055021) (0.46 g, 1 mmol) in 25 mL dry THF. After 5 min the cooling bath is removed and the reaction mixture is heated to RT. Then while cooling, 1 mL of water is added dropwise and the mixture is stirred for 30 min. The precipitate is filtered and the filtrate evaporated down.
Yield: 0.34 g.

Z-6) 1-(4-dimethylaminomethyl-phenyl)-3-pyridin-3-yl-4,5-dihydro-1H-pyrazolo[4,3-g]benzothiazol-7-ylamine

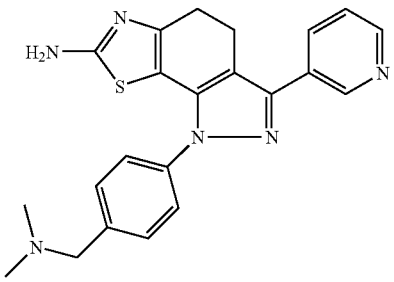

The desired product is obtained analogously to the preparation of Z-5 starting from 4-(7-amino-3-pyridin-3-yl-4,5-dihydro-pyrazolo[4,3-g]benzothiazol-1-yl)-N,N-dimethyl-benzamide (PCT/EP05055021) (1.4 g, 3.4 mmol) and lithium aluminium hydride (1 M in THF, 6 mL). Yield: 1.4 g (w=0.9).

Z-7) 1-(2-chloro-4-piperidin-1-ylmethylphenyl)-3-pyridin-3-yl-4,5-dihydro-1H-pyrazolo[4,3-g]benzothiazol-7-ylamine

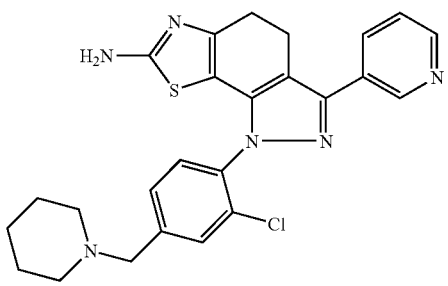

Z-7a) [4-(7-amino-3-pyridin-3-yl-4,5-dihydro-pyrazolo[4,3-g]benzothiazol-1-yl)-3-chlorophenyl]-piperidin-1-yl-methanone

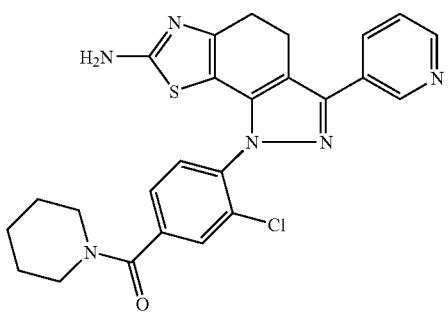

N,N-diisopropylethylamine (0.42 mL, 2.4 mmol) is added to a solution of 4-(7-amino-3-pyridin-3-yl-4,5-dihydro-pyrazolo[4,3-g]benzothiazol-1-yl)-3-chlorobenzoic acid (PCT/EP05055021) (0.25 g, 0.5 mmol) and O-(7-azabenzotriazol-1-yl)-N,N,N',N'-tetramethyluronium hexafluorophosphate (0.24 g, 0.6 mmol) in 10 mL dichloromethane and the mixture is stirred for 1 h at RT. Then piperidine (60 µL, 0.6 mmol) is added and the mixture is stirred overnight at RT. The reaction mixture is evaporated down, dissolved in 2 mL DMF and purified by RP-HPLC chromatography. Yield: 94 mg.

Under an argon atmosphere borane-THF complex (1 M in THF, 1.81 mL) is added to a solution of Z-7a (89 mg, 0.18 mmol) in 8 mL dry THF and the reaction mixture is stirred for 13 h at 60° C. Then 5 mL TMEDA is added and the reaction mixture is evaporated down. The residue is dissolved in 2 mL DMF, filtered and purified by RP-HPLC chromatography. Yield: 15 mg.

Z-8) N-[1-(2-fluoro-5-formylphenyl)-3-pyridin-3-yl-4,5-dihydro-1H-pyrazolo[4,3-g]benzothiazol-7-yl]-acetamide

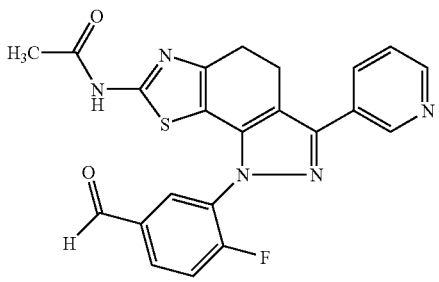

Z-8a) N-[1-(5-cyano-2-fluoro-phenyl)-3-pyridin-3-yl-4,5-dihydro-1H-pyrazolo[4,3-g]benzothiazol-7-yl]-acetamide

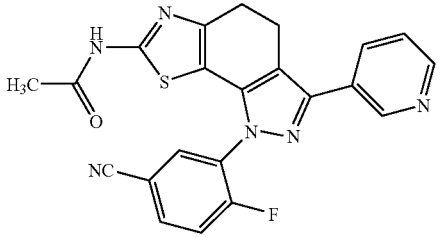

The desired compound I-9 is obtained analogously to the preparation of I-1 starting from Z-1 (4.7 g, 15 mmol), H-8 (4.1 g, 15.1 mmol) and 170 mL glacial acetic acid compound.

Yield: 4.8 g (w=0.8)

A solution of Z-8a (400 mg, w=0.7, 0.65 mmol) in 3 mL pyridine and 1.4 mL acetic acid is stirred for 30 min at RT, combined with Raney nickel (400 mg, 6.8 mmol) and stirred for 1 h at 60° C. Then it is filtered through Celite, washed with pyridine and the filtrate is evaporated down in vacuo. The residue is taken up in DMF and purified by RP-chromatography. Yield: 122 mg.

EXAMPLE 1.1

N-[1-(4-azetidin-1-ylmethyl-2-chlorophenyl)-3-pyridin-3-yl-4,5-dihydro-1H-pyrazolo[4,3-g]benzothiazol-7-yl]-acetamide A solution of Z-3 (0.1 g, 0.16 mmol) and azetidine (12 µL, 0.18 mmol) in 4 mL dichloromethane is stirred for 1.5 h at RT. Then sodium trisacetoxyborohydride (40 mg, 19 mmol) is added and the mixture is stirred for 2 d at RT. The reaction mixture is evaporated down, the residue is dissolved in 2 mL DMF and purified by RP-HPLC chromatography.

Yield: 28 mg.

Examples 1.2-1.8 are prepared analogously to the synthesis of 2.1.

| # | educt | structure | mass [M + 1]⁺ | HPLC:Rt [min] |
|---|---|---|---|---|
| 1.1 | Z-3 | 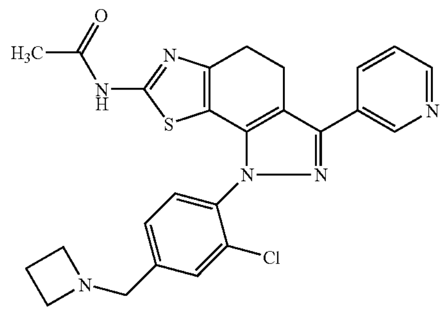 | 491 | 0.58 |
| 1.2 | Z-3 | 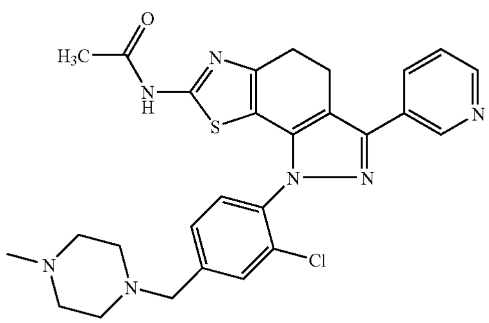 | 534 | 1.30 |
| 1.3 | Z-3 | 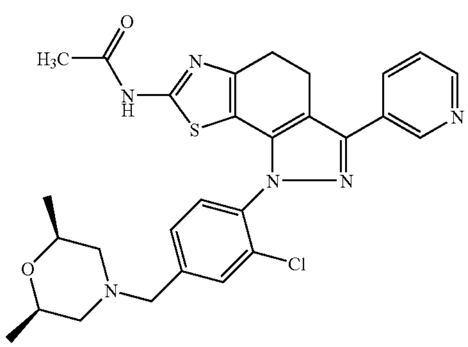 | 549 | 1.33 |
| 1.4 | Z-3 | 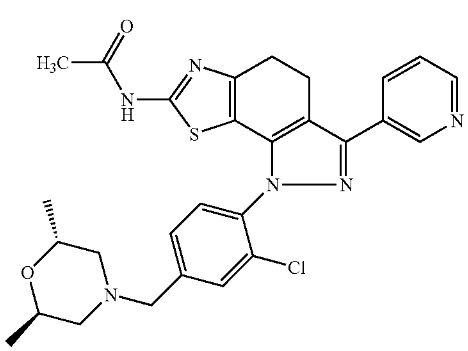 | 549 | 1.35 |

| # | educt | structure | mass [M + 1]+ | HPLC:Rt [min] |
|---|---|---|---|---|
| 1.5 | Z-3 | 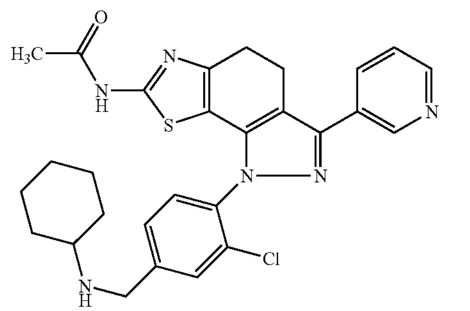 | 533 | 0.74 |
| 1.6 | Z-3 | 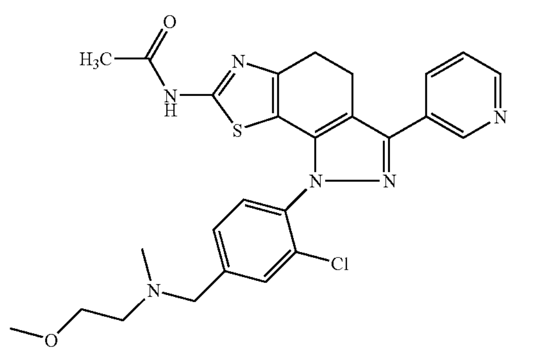 | 523 | 1.27 |
| 1.7 | Z-3 | 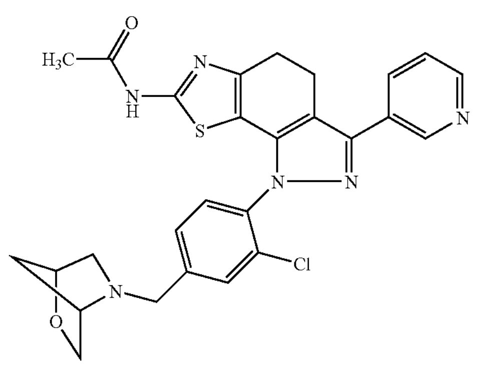 | 533 | 0.51 |
| 1.8 | Z-4 | 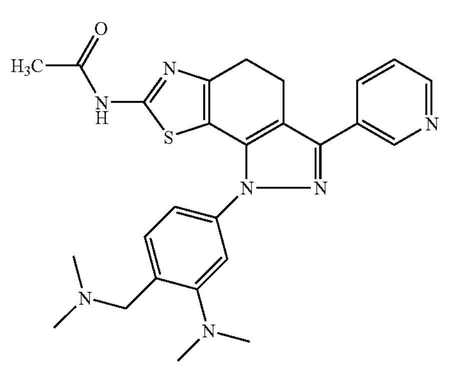 | 488 | 1.35 |

EXAMPLE 2.1

N-{1-[4-(1-morpholin-4-yl-cyclopropyl)-phenyl]-3-pyridin-3-yl-4,5-dihydro-1H-pyrazolo[4,3-g]benzothiazol-7-yl}-acetamide A solution of Z-1 (0.13 g, 0.4 mmol) and H-4 (0.18 g, 0.52 mmol) in 5 mL glacial acetic acid is stirred overnight at RT.

The reaction mixture is evaporated down, the residue is dissolved in 2 mL DMSO and purified by RP-HPLC. Yield: 15 mg.

Examples 2.2-2.5 are prepared analogously to the synthesis of 2.1.

| # | educt | structure | mass [M + 1]$^+$ | HPLC:Rt [min] |
|---|---|---|---|---|
| 2.1 | Z-1<br>H-4 | 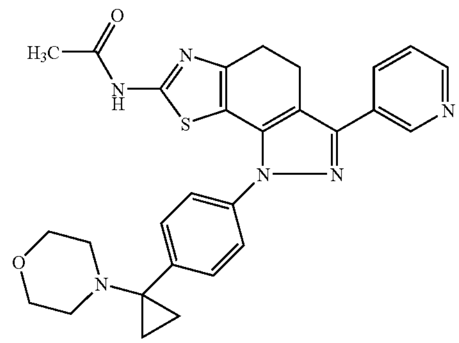 | 513 | 1.42 |
| 2.2 | Z-1<br>H-3 | 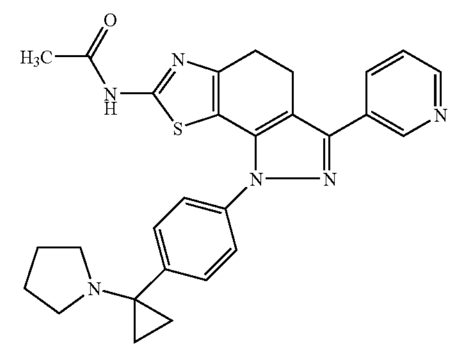 | 497 | 1.42 |
| 2.3 | Z-1<br>H-2 | 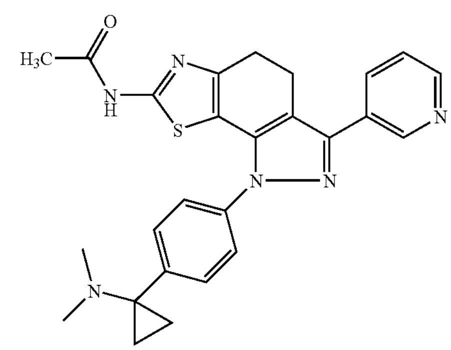 | 471 | 1.23 |
| 2.4 | Z-2<br>H-2 | 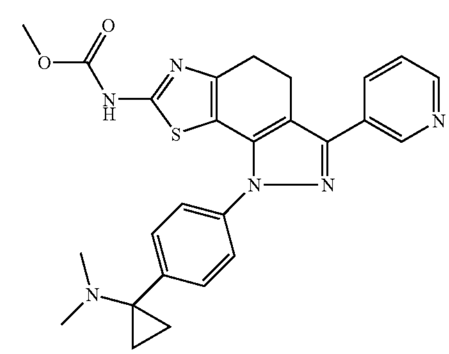 | 487 | 1.27 |

| # | educt | structure | mass [M + 1]⁺ | HPLC:Rt [min] |
|---|---|---|---|---|
| 2.5 | Z-1<br>H-5 | (structure) | 468 | 1.22 |

EXAMPLE 2.6

N-[1-(2-chloro-4-morpholin-4-ylmethyl-phenyl)-3-pyridin-3-yl-4,5-dihydro -1H-pyrazolo[4,3-g]benzothiazol-7-yl]-acetamide A solution of Z-1 (4.6 g, 15 mmol) and H-1 (4.7 g, 15 mmol) in 54 mL ethanol is heated in the microwave for 10-12 min at 120-135° C. in three parts. The precipitate formed is filtered and washed with ethanol. Yield: 4.3 g.

Example 2.7 is prepared analogously to the synthesis of 2.6.

EXAMPLE 3.1

N-[1-(2-chloro-4-dimethylaminomethyl-phenyl)-3-pyridin-3-yl-4,5-dihydro -1H-pyrazolo[4,3-g]benzothiazol-7-yl]-acetamide Pyridine (0.4 mL, 40 mmol) and acetyl chloride (0.32 mL, 4 mmol) are added to a solution of Z-5 (0.18 g, 0.4 mmol) in 50 mL dichloromethane and the reaction mixture is stirred for 1 h at RT. Then 2 mL methanol is added and the reaction mixture is evaporated down. The residue is dissolved in 2 mL DMSO and purified by chromatography using RP-HPLC and then on silica gel with dichloromethane/methanol. Yield: 35 mg.

| # | educt | structure | mass [M + 1]⁺ | HPLC:Rt [min] |
|---|---|---|---|---|
| 2.6 | Z-1<br>H-1 | (structure) | 521 | 0.55 |
| 2.7 | Z-2<br>H-1 | (structure) | 537 | 1.26 |

Examples 3.2 and 3.3 are prepared analogously to the synthesis of 3.1.
| # | educt | structure | mass [M + 1]⁺ | HPLC:Rt [min] |
|---|---|---|---|---|
| 3.1 | Z-5 | 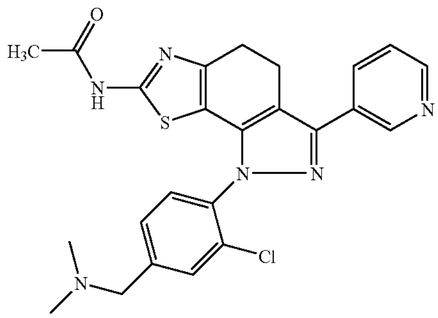 | 479 | 0.50 |
| 3.2 | Z-6 | 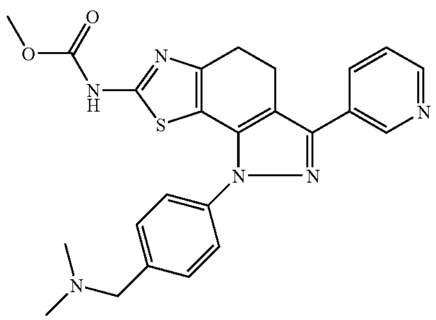 | 461 | 1.28 |
| 3.3 | Z-7 | 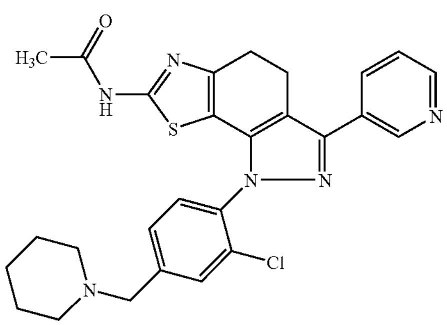 | 519 | 1.32 |
EXAMPLE 4
1-[1-(2-chloro-4-dimethylaminomethyl-phenyl)-3-pyridin-3-yl-4,5-dihydro-1H-pyrazolo[4,3-g]benzothiazol-7-yl]-3-methyl-urea
4-a) methyl 3-chloro-4-(7-ethylsulphanylcarbonylamino-3-pyridin-3-yl-4,5-dihydro-pyrazolo[4,3-g]benzothiazol-1-yl)-benzoate
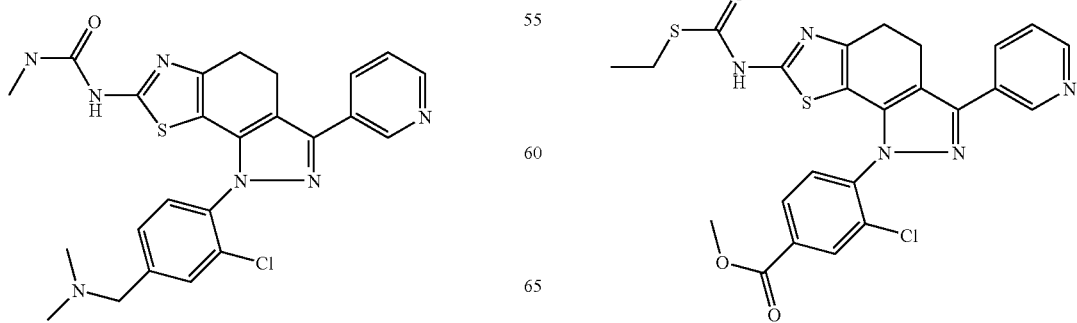

A solution of S-ethyl [7-oxo-6-(pyridine-3-carbonyl)-4,5,6,7-tetrahydro-benzothiazol-2-yl]-thiocarbamidate (PCT/EP05055021) (3.6 g, 10 mmol) and methyl 3-chloro-4-hydrazino-benzoate (3.7 g, 18 mmol) in 100 mL glacial acetic acid is stirred overnight at 50° C., then added to water and the precipitate formed is filtered off. Yield 2.9 g.

4-b) 3-chloro-4-(7-ethylsulphanylcarbonylamino-3-pyridin-3-yl-4,5-dihydro-pyrazolo[4,3-g]benzothiazol-1-yl)-benzoic acid

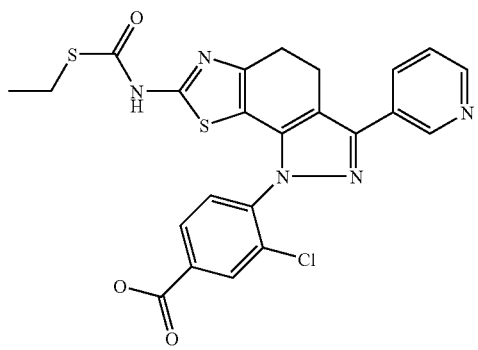

A suspension of 4-a (5.3 g, 10 mmol) in 20 mL dioxane is combined with lithium hydroxide (3.2 g, in 50 mL water). After the solution has cleared the reaction mixture is stirred for another 30 mm at RT and combined with 5 M hydrochloric acid. The precipitate formed is filtered, washed with water and dried. Yield: 3.8 g.

4-c) S-ethyl [1-(2-chloro-4-dimethylcarbamoylphenyl)-3-pyridin-3-yl-4,5-dihydro-1H-pyrazolo[4,3-g]benzothiazol-7-yl]-thiocarbamidate

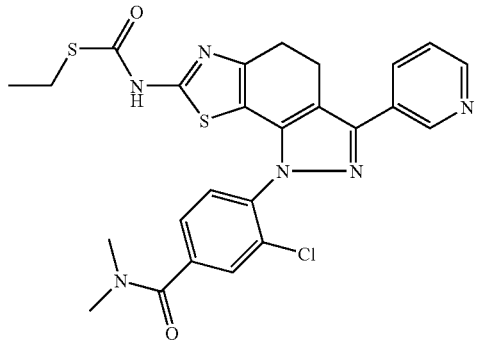

Dimethylamine (2 M in THF, 0.6 mL) is added to a solution of 4-b (0.52 g, 1 mmol), O-benzotriazol-1-yl-N,N,N',N'-tetramethyluronium tetrafluoroborate (0.38 g, 1.1 mmol) and N,N-diisopropylethylamine (0.6 mL, 6.3 mmol) in 10 on of THF and the mixture is stirred overnight at RT. Then the reaction mixture is mixed with water and extracted with ethyl acetate. The combined organic phases are dried and evaporated down. Yield: 0.54 μg 4-d) 3-chloro-N,N-dimethyl-4-[7-(3-methyl-ureido)-3-pyridin-3-yl-4,5-dihydro-pyrazolo[4,3-g]benzothiazol-1-yl]-benzamide

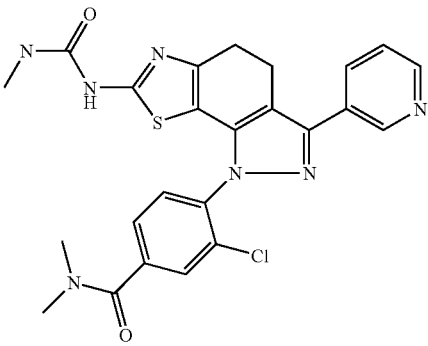

A solution of 4-c (0.5 g, 0.46 mmol) and methylamine (2 M in THF, 2 mL) in 40 mL dichloromethane/THF is stirred overnight at 80° C. The reaction mixture is evaporated down, the residue is dissolved in DMF and purified by RP-HPLC chromatography. Yield: 0.10 g.

Lithium aluminium hydride (1 M in THF, 0.5 mL) is added to a solution of 4-d (0.1 g, 0.2 mmol) in 10 mL dry THF under an argon atmosphere at −78° C. After the removal of the cooling bath the reaction mixture is stirred for 1.5 h at RT and then mixed with water. The reaction mixture is evaporated down, the residue is dissolved in DMF and purified by RP-HPLC chromatography. Yield: 30 mg.

HPLC: Rt=0.59 min

[M+1]$^+$=494

EXAMPLE 5.1

N-{1-[2-fluoro-5-(4-methylpiperazin-1-ylmethyl)-phenyl]-3-pyridin-3-yl -4,5-dihydro-1H-pyrazolo[4,3-g]benzothiazol-7-yl}-acetamide

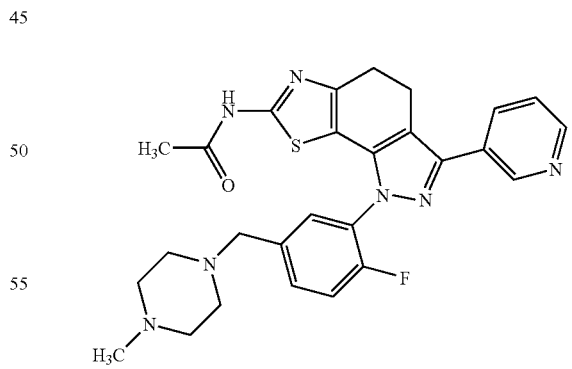

A suspension of Z-8 (50 mg, 0.11 mmol) in 1 mL 1,2-dichloroethane is combined with N-methylpiperazine (19 mL, 0.17 mmol) and stirred for 1 h at RT. Then 10 μL glacial acetic acid and sodium trisacetoxyborohydride (37 mg, 0.17 mmol) are added successively. After the reaction is complete (HPLC) the reaction mixture is purified by chromatography. Yield: 32 mg.

EXAMPLE 5.2
The following Examples are synthesised analogously to Example 5.1
| # | educt | structure | mass [M + 1]⁺ | HPLC Rt [min] |
|---|---|---|---|---|
| 5.1 | Z-8 | 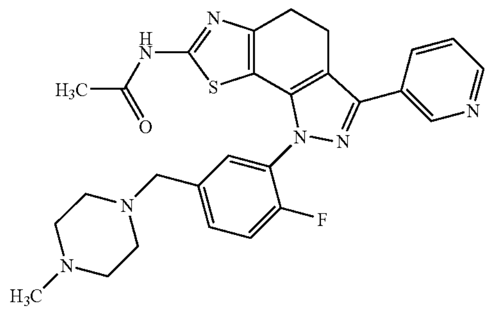 | 518 | 1.33 |
| 5.2 | Z-8 | 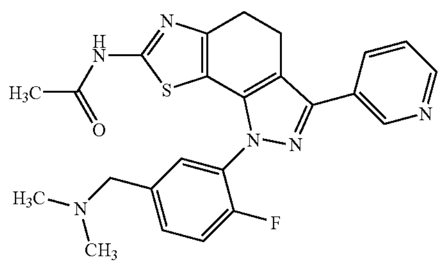 | 463 | 1.25 |
In addition, the following compounds may be prepared using the methods described above.
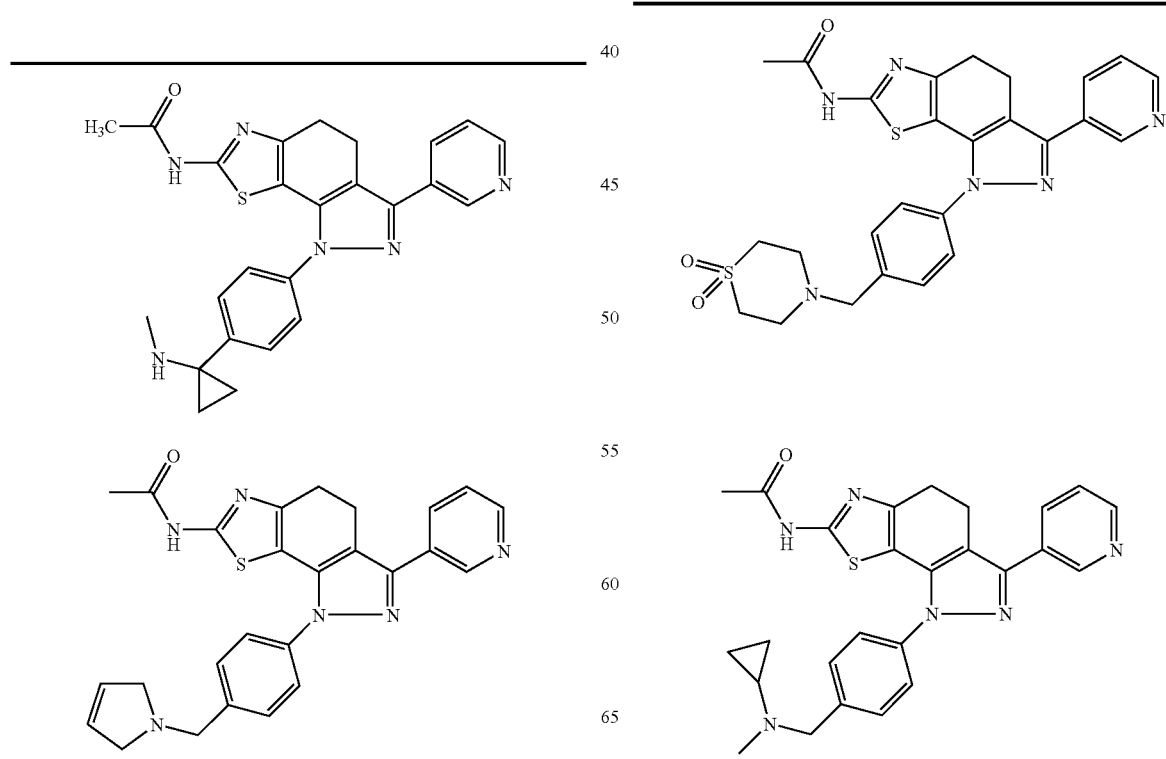

-continued
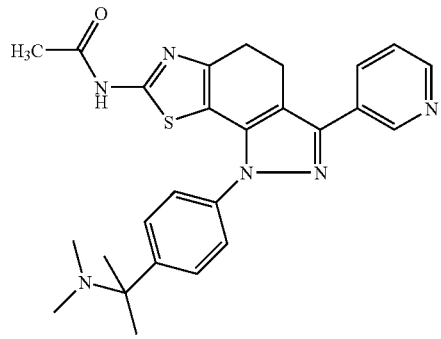
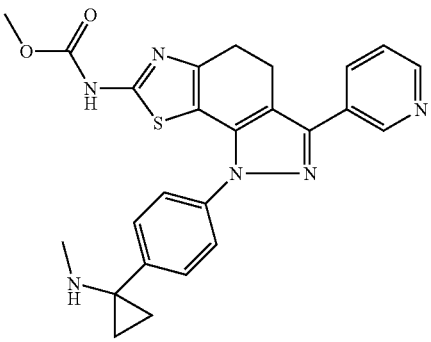
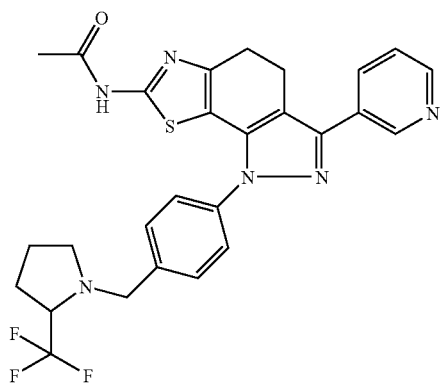
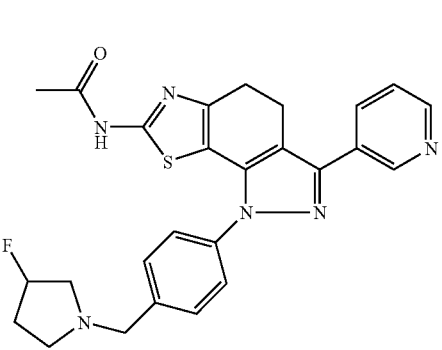
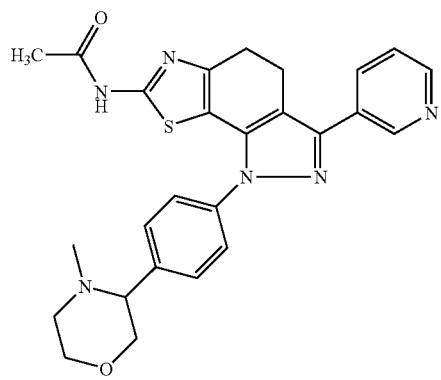
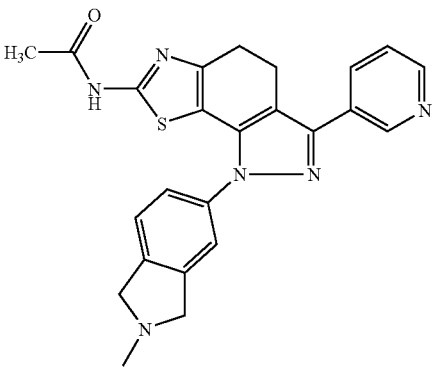
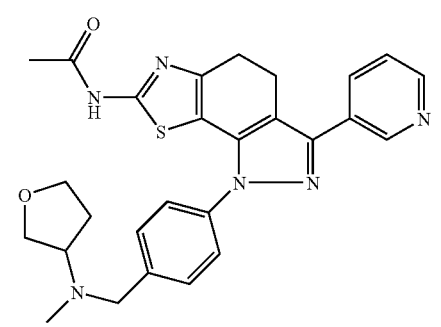
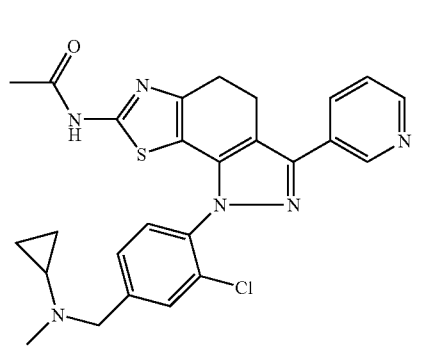

| 41 | 42 |
|---|---|
| -continued | -continued |
| 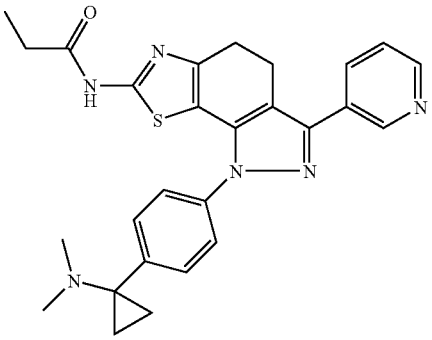 | 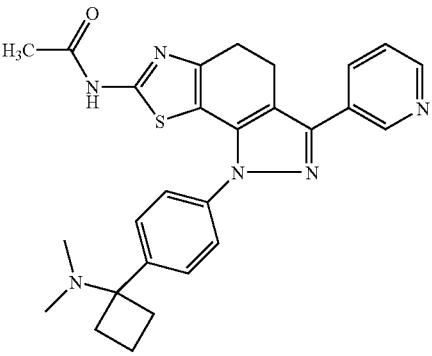 |
| 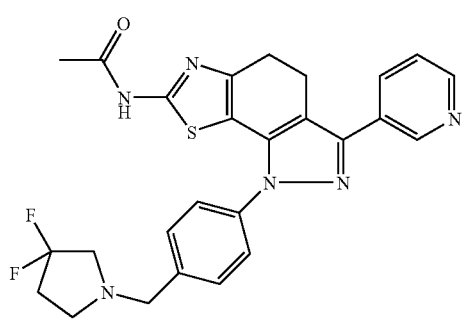 | 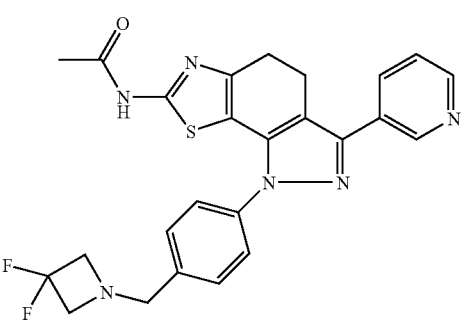 |
| 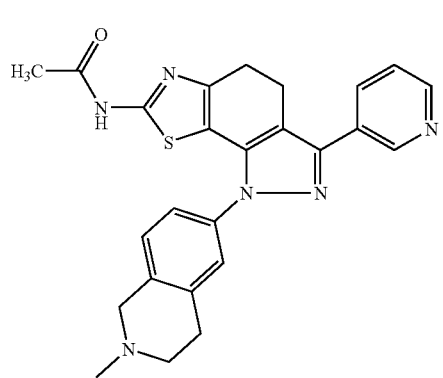 | 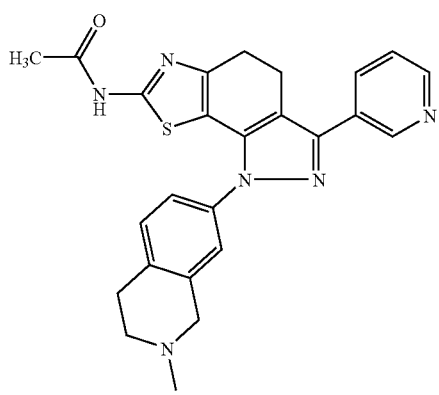 |
| 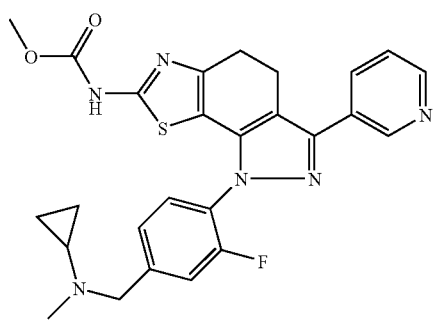 | 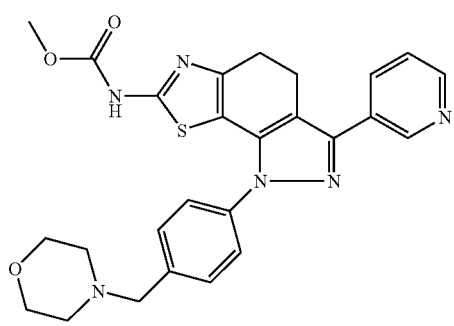 |

-continued
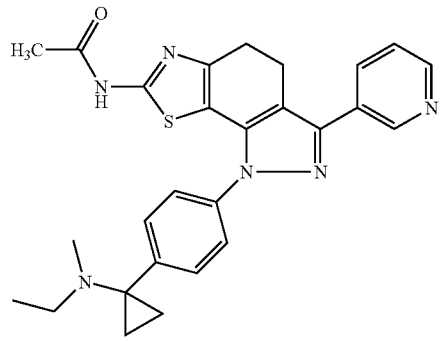
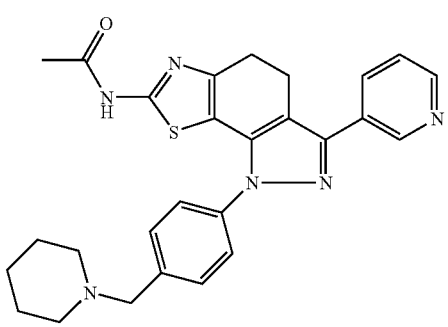
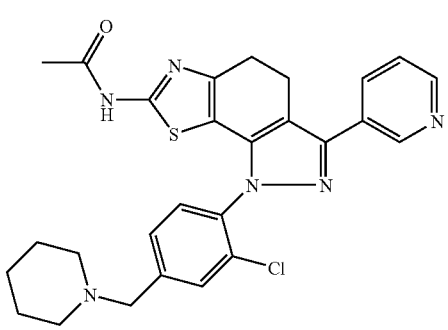
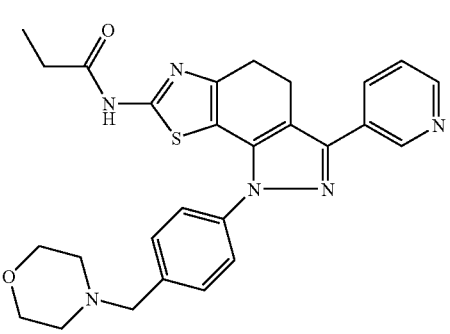
-continued
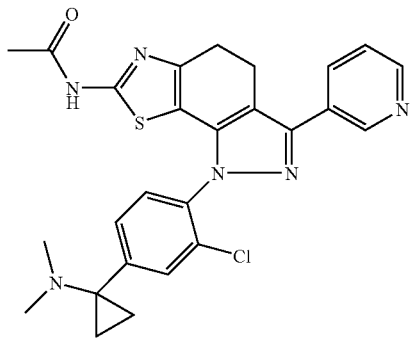
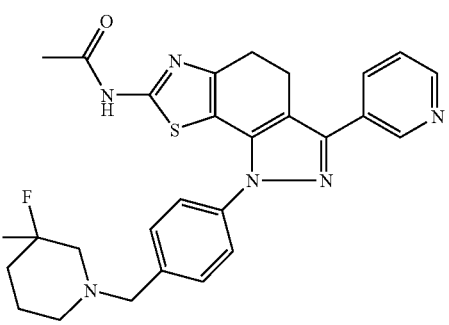
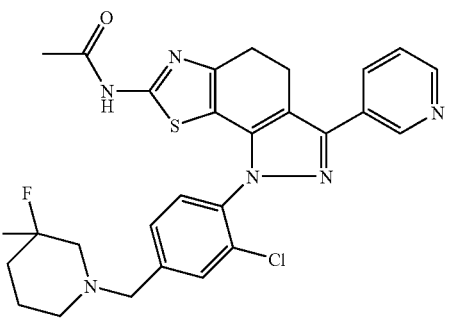
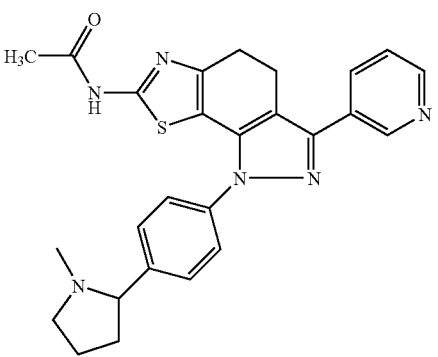

-continued

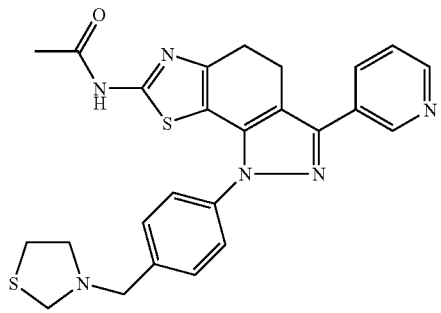

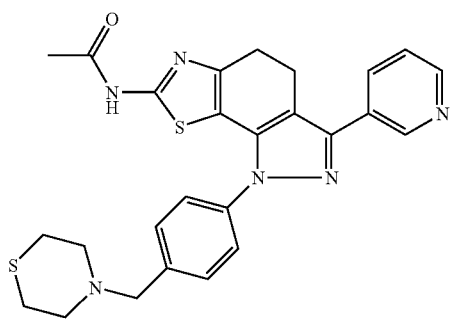

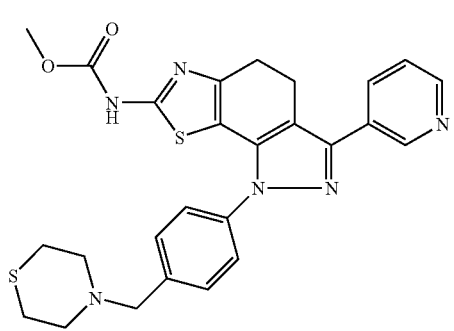

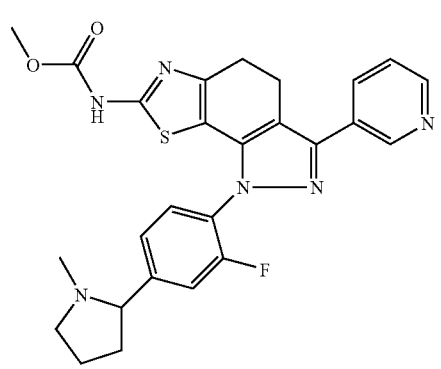

-continued

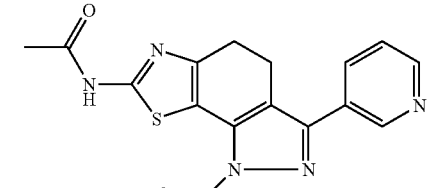

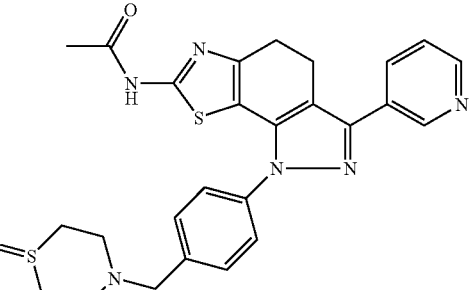

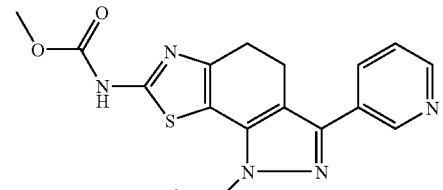

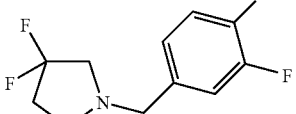

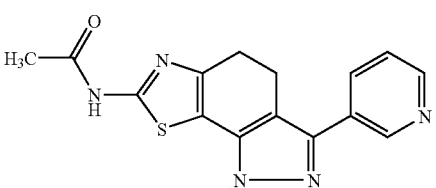

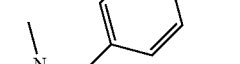

The Example that follows describes the biological activity of the compounds according to the invention without restricting the invention to this Example.

HCT116 Cytotoxicity Test

The test is based on the reduction of AlamarBlue (Biosource Int., USA) in living (metabolically active) cells to give a fluorometrically detectable product. The substrate can no longer be reduced in the presence of substances which are toxic to the cells, which means that it is not possible to measure any increase in fluorescence.

HCT 116 (human colon carcinoma cell line) cells are sown in microtitre plates and incubated overnight in culture medium at 37° C. and 5% $CO_2$. The test substances are diluted stepwise in medium and added to the cells such that the total volume is 200 μl/well. Cells to which medium, but not substance, is added serve as controls. After an incubation time of 4-6 days, 20 μl of AlamarBlue are added/well and the cells are incubated at 37° C. for a further 6-8 h. For measuring the fluorescence, excitation takes place at a wavelength of 545 nm and the emission is measured at 590 nm.

$EC_{50}$ values are calculated using the GraphPad Prism program.

All the compounds of Examples 1.1 to 5.2 cited have an $EC_{50}$ (HCT-116) of less than 5 μM.

The substances of the present invention are PI3 kinase inhibitors. On account of their biological properties, the novel compounds of the general formula (1) and their isomers and their physiologically tolerated salts are suitable for treating diseases which are characterized by excessive or anomalous cell proliferation.

These diseases include, for example: viral infections (e.g. HIV and Kaposi's sarcoma); inflammation and autoimmune diseases (e.g. colitis, arthritis, Alzheimer's disease, glomerulonephritis and wound healing); bacterial, fungal and/or parasitic infections; leukaemias, lymphomas and solid tumours; skin diseases (e.g. psoriasis); bone diseases; cardiovascular diseases (e.g. restenosis and hypertrophy). In addition, the compounds are useful for protecting proliferating cells (e.g. hair cells, intestinal cells, blood cells and progenitor cells) from DNA damage due to irradiation, UV treatment and/or cytostatic treatment (Davis et al., 2001).

For example, the following cancer diseases can be treated with compounds according to the invention, without, however, being restricted thereto: brain tumours, such as acoustic neurinoma, astrocytomas such as piloid astrocytomas, fibrillary astrocytoma, protoplasmic astrocytoma, gemistocytic astrocytoma, anaplastic astrocytoma and glioblastomas, brain lymphomas, brain metastases, hypophyseal tumour such as prolactinoma, HGH (human growth hormone) producing tumour and ACTH-producing tumour (adrenocorticotrophic hormone), craniopharyngiomas, medulloblastomas, meningiomas and oligodendrogliomas; nerve tumours (neoplasms) such as tumours of the vegetative nervous system such as neuroblastoma sympathicum, ganglioneuroma, paraganglioma (phaeochromocytoma and chromaffinoma) and glomus caroticum tumour, tumours in the peripheral nervous system such as amputation neuroma, neurofibroma, neurinoma (neurilemoma, schwannoma) and malignant schwannoma, as well as tumours in the central nervous system such as brain and spinal cord tumours; intestinal cancer such as rectal carcinoma, colon carcinoma, anal carcinoma, small intestine tumours and duodenal tumours; eyelid tumours such as basalioma or basal cell carcinoma; pancreatic gland cancer or pancreatic carcinoma; bladder cancer or bladder carcinoma; lung cancer (bronchial carcinoma) such as small-cell bronchial carcinomas (oat cell carcinomas) and non-small-cell bronchial carcinomas such as squamous epithelium carcinomas, adenocarcinomas and large-cell bronchial carcinomas; breast cancer such as mammary carcinoma, such as infiltrating ductal carcinoma, colloid carcinoma, lobular invasive carcinoma, tubular carcinoma, adenoid cystic carcinoma, and papillary carcinoma; non-Hodgkin's lymphomas (NHL) such as Burkitt's lymphoma, low-malignancy non-Hodgkin's lymphomas (NHL) and mucosis fungoides; uterine cancer or endometrial carcinoma or corpus carcinoma; CUP syndrome (cancer of unknown primary); ovarian cancer or ovarian carcinoma such as mucinous, endometrial or serous cancer; gall bladder cancer; bile duct cancer such as Klatskin's tumour; testicular cancer such as seminomas and non-seminomas; lymphoma (lymphosarcoma) such as malignant lymphoma, Hodgkin's disease, non-Hodgkin's lymphomas (NHL) such as chronic lymphatic leukaemia, hair cell leukaemia, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as vocal cord tumours, supraglottal, glottal and subglottal laryngeal tumours; bone cancer such as osteochondroma, chondroma, chrondoblastoma, chondromyxoidfibroma, osteoma, osteoid-osteoma, osteoblastoma, eosinophilic granuloma, giant cell tumour, chondrosarcoma, osteosarcoma, Ewing's sarcoma, reticulosarcoma, plasmocytoma, fibrous dysplasia, juvenile bone cyst and aneurysmatic bone cyst; head/neck tumours such as tumours of the lips, tongue, floor of the mouth, oral cavity, gingiva, pallet, salivary glands, pharynx, nasal cavities, paranasal sinuses, larynx and middle ear; liver cancer such as liver cell carcinoma or hepatocellular carcinoma (HCC); leukaemias, such as acute leukaemias, such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or stomach carcinoma such as papillary, tubular and mucinous adenocarcinoma, signet ring cell carcinoma, adenoid squamous cell carcinoma, small-cell carcinoma and undifferentiated carcinoma; melanomas such as superficially spreading, nodular malignant lentigo and acral lentiginous melanoma; renal cancer, such as kidney cell carcinoma or hypernephroma or Grawitz's tumour; oesophageal cancer or oesophageal carcinoma; cancer of the penis; prostate cancer; pharyngeal cancer or pharyngeal carcinomas such as nasopharyngeal carcinomas, oropharyngeal carcinomas and hypopharyngeal carcinomas; retinoblastoma such as vaginal cancer or vaginal carcinoma; squamous epithelium carcinomas, adeno carcinomas, in situ carcinomas, malignant melanomas and sarcomas; thyroid gland carcinomas such as papillary, follicular and medullary thyroid gland carcinoma, and also anaplastic carcinomas; spinalioma, prickle cell carcinoma and squamous epithelium carcinoma of the skin; thymomas, urethral cancer and vulvar cancer.

The novel compounds can be used for the prevention or short-term or long-term treatment of the abovementioned diseases including, where appropriate, in combination with other state-of-the-art compounds such as other anti-tumour substances, cytotoxic substances, cell proliferation inhibitors, antiangiogenic substances, steroids or antibodies.

The compounds of the general formula (1) can be used on their own or in combination with other active compounds according to the invention and, where appropriate, in combination with other pharmacologically active compounds as well. Chemotherapeutic agents which can be administered in combination with the compounds according to the invention include, without being restricted thereto, hormones, hormone analogs and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone and octreotide), aromatase inhibitors (e.g. anastrozole, letrozole, liarozole, vorozole, exemestane and atamestane), LHRH agonists and antagonists (e.g. goserelin acetate and luprolide), inhibitors of growth factors (growth factors such as platelet-derived growth factor and hepatocyte growth factor, examples of inhibitors are growth factor antibodies, growth factor receptor antibodies and tyrosine kinase inhibitors, such as gefitinib, imatinib, lapatinib, Erbitux® and trastuzumab); antimetabolites (e.g. antifolates such as methotrexate and raltitrexed, pyrimidine analogs such as 5-fluorouracil, capecitabine and gemcitabine, purine and adenosine analogs such as mercaptopurine, thioguanine, cladribine and pentostatin, cytarabine and fludarabine); antitumour antibiotics (e.g. anthracyclines, such as doxorubicin, daunorubicin, epirubicin and idarubicin, mitomycin C, bleomycin, dactinomycin, plicamycin and streptozocin); platinum derivatives (e.g. cisplatin, oxaliplatin and carboplatin); alkylating agents (e.g. estramustine, meclorethamine, melphalan, chlorambucil, busulphan, dacarbazine, cyclophosphamide, ifosfamide and temozolomide, nitrosoureas such as carmustine and lomustine and thiotepa); antimitotic agents (e.g. vinca alkaloids such as vinblastine, vindesine, vinorelbine and vincristine; and taxans such as paclitaxel and docetaxel); topoisomerase inhibitors (e.g. epipodophyllotoxins such as etoposide and etopophos, teniposide, amsacrine, topotecan, irinotecan and mitoxantrone) and various chemotherapeutic agents such as amifostin, anagrelide, clodronate, filgrastin, interferon alpha, leucovorin, rituximab, procarbazine, levamisole, mesna, mitotan, pamidronate and porfimer.

Examples of suitable forms for use are tablets, capsules, suppositories, solutions, in particular solutions for injection (s.c., i.v., i.m.) and infusion, syrups, emulsions or dispersible powders. In this connection, the proportion of the pharmaceutically active compound(s) should in each case be in the range of 0.1-90% by weight, preferably 0.5-50% by weight, of the total composition, that is in quantities which are sufficient to achieve the dosage range which is specified below. If necessary, the doses mentioned can be given several times a day.

Appropriate tablets can be obtained, for example, by mixing the active compound(s) with known auxiliary substances, for example inert diluents, such as calcium carbonate, calcium phosphate or lactose, disintegrants, such as maize starch or alginic acid, binders, such as starch or gelatine, lubricants, such as magnesium stearate or talc, and/or agents for achieving a depot effect, such as carboxymethyl cellulose, cellulose acetate phthalate or polyvinyl acetate. The tablets can also comprise several layers.

Correspondingly, sugar-coated tablets can be produced by coating cores, which have been prepared in analogy with tablets, with agents which are customarily used in sugar coatings, for example collidone or shellac, gum arabic, talc, titanium dioxide or sugar. The core can also comprise several layers in order to achieve a depot effect or to avoid incompatibilities. In the same way, the sugar coating can also comprise several layers in order to achieve a depot effect, with it being possible to use the auxiliary substances which are mentioned above in the case of the tablets.

Syrups of the active compounds or active compound combinations according to the invention can additionally comprise a sweetening agent, such as saccharine, cyclamate, glycerol or sugar as well as a taste-improving agent, e.g. flavouring agents such as vanillin or orange extract. They can also comprise suspension aids or thickeners, such as sodium carboxymethyl cellulose, wetting agents, for example condensation products of fatty alcohols and ethylene oxide, or protectants such as p-hydroxybenzoates.

Injection and infusion solutions are produced in a customary manner, e.g. while adding isotonizing agents, preservatives, such as p-hydroxybenzoates, or stabilizers, such as alkali metal salts of ethylenediaminetetraacetic acid, where appropriate using emulsifiers and/or dispersants, with it being possible, for example, to employ, where appropriate, organic solvents as solubilizing agents or auxiliary solvents when using water as diluent, and aliquoted into injection bottles or ampoules or infusion bottles.

The capsules, which comprise one or more active compounds or active compound combinations, can, for example, be produced by mixing the active compounds with inert carriers, such as lactose or sorbitol, and encapsulating the mixture in gelatine capsules. Suitable suppositories can be produced, for example, by mixing with excipients which are envisaged for this purpose, such as neutral fats or polyethylene glycol, or their derivatives.

Auxiliary substances which may be mentioned by way of example are water, pharmaceutically unobjectionable organic solvents, such as paraffins (e.g. petroleum fractions), oils of vegetable origin (e.g. groundnut oil or sesame oil), monofunctional or polyfunctional alcohols (e.g. ethanol or glycerol), carrier substances such as natural mineral powders (e.g. kaolins, argillaceous earths, talc and chalk), synthetic mineral powders (e.g. highly disperse silicic acid and silicates), sugars (e.g. cane sugar, lactose and grape sugar), emulsifiers (e.g. lignin, sulphite waste liquors, methyl cellulose, starch and polyvinylpyrrolidone) and glidants (e.g. magnesium stearate, talc, stearic acid and sodium lauryl sulphate).

Administration is effected in a customary manner, preferably orally or transdermally, in particular and preferably orally. In the case of oral use, the tablets can naturally also comprise, in addition to the abovementioned carrier substances, additives such as sodium citrate, calcium carbonate and dicalcium phosphate together with a variety of further substances such as starch, preferably potato starch, gelatine and the like. It is furthermore also possible to use glidants, such as magnesium stearate, sodium lauryl sulphate and talc, for the tableting. In the case of aqueous suspensions, a variety of taste improvers or dyes can also be added to the active compounds in addition to the abovementioned auxiliary substances.

For parenteral administration, it is possible to employ solutions of the active compounds while using suitable liquid carrier materials. The dosage for intravenous administration is 1-1000 mg per hour, preferably between 5 and 500 mg per hour.

Despite this, it may be necessary, where appropriate, to diverge from the abovementioned quantities, depending on the body weight or the nature of the route of administration, on the individual response to the medicament, on the nature of its formulation and on the time or interval at which the administration is effected. Thus, it may, in some cases, be sufficient to make do with less than the previously mentioned lowest quantity whereas, in other cases, the abovementioned upper limit has to be exceeded. When relatively large quantities are being administered, it may be advisable to divide these into several single doses which are given over the course of the day.

The following formulation examples illustrate the present invention without, however, restricting its scope:

PHARMACEUTICAL FORMULATION
EXAMPLES

| A) Tablets | per tablet |
| --- | --- |
| Active compound in accordance with formula (1) | 100 mg |
| Lactose | 140 mg |
| Maize starch | 240 mg |
| Polyvinylpyrrolidone | 15 mg |
| Magnesium stearate | 5 mg |
| | 500 mg |

The finely ground active compound, lactose and a part of the maize starch are mixed with each other. The mixture is sieved, after which it is moistened with a solution of polyvinylpyrrolidone in water, kneaded, wet-granulated and dried. The granular material, the remainder of the maize starch and the magnesium stearate are sieved and mixed with each other. The mixture is pressed into tablets of suitable shape and size.

| B) Tablets | per tablet |
|---|---|
| Active compound in accordance with formula (1) | 80 mg |
| Lactose | 55 mg |
| Maize starch | 190 mg |
| Microcrystalline cellulose | 35 mg |
| Polyvinylpyrrolidone | 15 mg |
| Sodium carboxymethyl starch | 23 mg |
| Magnesium stearate | 2 mg |
| | 400 mg |

The finely ground active compound, a part of the maize starch, the lactose, microcrystalline cellulose and polyvinylpyrrolidone are mixed with each other, after which the mixture is sieved and worked, together with the remainder of the maize starch and water, into a granular material, which is dried and sieved. The sodium carboxymethyl starch and the magnesium stearate are then added to the granular material and mixed with it, and the mixture is pressed into tablets of suitable size.

| C) Ampoule solution | |
|---|---|
| Active compound in accordance with formula (1) | 50 mg |
| Sodium chloride | 50 mg |
| Water for injection | 5 ml |

The active compound is dissolved, either at its intrinsic pH or, where appropriate, at pH 5.5-6.5, in water after which sodium chloride is added as isotonizing agent. The resulting solution is rendered pyrogen-free by filtration and the filtrate is aliquoted, under aseptic conditions, into ampoules, which are then sterilized and sealed by melting. The ampoules contain 5 mg, 25 mg and 50 mg of active compound.

What is claimed is:

1. A compound of formula (1),

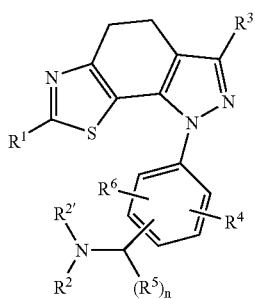

wherein $R^1$ is selected from among —NHR$^a$, —NHC(O)R$^a$, —NHC(O)OR$^a$, —NHC(O)NR$^a$R$^a$ and —NHC(O)SR$^a$, and $R^2$ and $R^{2'}$ each independently of one another denote hydrogen or a group selected from among $C_{1-6}$alkyl, $C_{3-8}$cycloalkyl, $C_{6-10}$aryl, 5-10 membered heteroaryl and 3-8 membered heterocycloalkyl, optionally substituted by one or more R$^a$ and/or R$^b$, or $R^2$ and $R^{2'}$ together with the enclosed nitrogen atom form a heterocycloalkyl or heteroaryl ring, which may optionally contain one or more further hetero atoms selected from among N, O and S and may optionally be substituted by one or more R$^b$ and/or R$^d$, and $R^3$ denotes a group selected from among $C_{6-10}$aryl and 5-6 membered heteroaryl, optionally substituted by one or more identical or different R$^c$ and/or R$^b$, and $R^4$ and $R^6$ each independently of one another denote hydrogen or a group selected from among halogen, —CF$_3$, —OCF$_3$, —CN, —NR$^c$R$^c$, —SR$^c$, —S(O)R$^c$, —S(O)$_2$R$^c$ and —OR$^c$, or $C_{1-3}$alkyl optionally substituted by fluorine, —CN, —NR$^f$R$^f$ and/or —OR$^f$, and $R^5$ $C_{1-3}$alkyl, or two $R^5$ together with the enclosed carbon atom form a $C_{3-8}$cycloalkyl ring or a 3-8 membered heterocycloalkyl, and n is equal to 0, 1 or 2, or $R^2$ together with an $R^5$ and the enclosed nitrogen and carbon atom form a 4-8 membered heterocycloalkyl ring, or $R^2$ together with a suitable $R^6$ and the enclosed nitrogen and carbon atoms form a 4-8 membered heterocycloalkyl ring, and each R$^a$ independently of one another denotes hydrogen or a group optionally substituted by one or more identical or different R$^b$ and/or R$^c$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and each R$^b$ denotes a suitable group each selected independently of one another from among =O, —OR$^c$, $C_{1-3}$haloalkyloxy, =S, —SR$^c$, =NR$^c$, =NOR$^c$, —NR$^c$R$^c$, halogen, —CF$_3$, —CN, —NC, —NO$_2$, —N$_3$, —S(O)R$^c$, —S(O)$_2$R$^c$, —S(O)$_2$OR$^c$, —S(O)NR$^c$R$^c$, —S(O)$_2$NR$^c$R$^c$, —OS(O)R$^c$, —OS(O)$_2$R$^c$, —OS(O)$_2$OR$^c$, —OS(O)$_2$NR$^c$R$^c$, —C(O)R$^c$, —C(O)OR$^c$, —C(O)NR$^c$R$^c$, —C(O)N(R$^d$)OR$^c$ —CN(R$^d$)NR$^c$R$^c$, —OC(O)R$^c$, —OC(O)OR$^c$, —OC(O)NR$^c$R$^c$, —OCN(R$^d$)NR$^c$R$^c$, —N(R$^d$)C(O)R$^c$, —N(R$^d$)C(S)R$^c$, —N(R$^d$)S(O)$_2$R$^c$, —N(R$^d$)C(O)OR$^c$, —N(R$^d$)C(O)NR$^c$R$^c$, and —N(R$^d$)CN(R$^d$)NR$^c$R$^c$, and each R$^c$ independently of one another denote hydrogen or a group optionally substituted by one or more identical or different R$^d$ selected from among $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, and each R$^d$ independently of one another denotes hydrogen, $C_{1-6}$alkyl, $C_{3-8}$cycloalkyl, $C_{4-11}$cycloalkylalkyl, $C_{6-10}$aryl, $C_{7-16}$arylalkyl, 2-6 membered heteroalkyl, 3-8 membered heterocycloalkyl, 4-14 membered heterocycloalkylalkyl, 5-10 membered heteroaryl and 6-16 membered heteroarylalkyl, or a pharmacologically acceptable salt thereof, with the proviso that following compounds are not included:

N-[1-(4-morpholin-4-ylmethyl-phenyl)-3-pyridin-2-yl-4,5-dihydro-1H-pyrazolo[4,3-g]benzothiazol-7-yl]-acetamide, N-[1-(4-dimethylaminomethyl-phenyl)-3-pyridin-3-yl-4,5-dihydro-1H-pyrazolo[4,3-g]benzothiazol-7-yl]-acetamide, N-{1-[4-(benzylamino-methyl)-2-chloro-phenyl]-3-pyrazin-2-yl-4,5-dihydro-1H-pyrazolo[4,3-g]benzothiazol-7-yl}-acetamide and N-(1-{2-chloro-4-[(1-cyclopentyl-piperidin-4-ylamino)-methyl]-phenyl}-3-pyrazin-2-yl-4,5-dihydro-1H-pyrazolo[4,3-g]benzothiazol-7-yl)-acetamide.

2. A compound of claim 1, which is of the formula (1A),

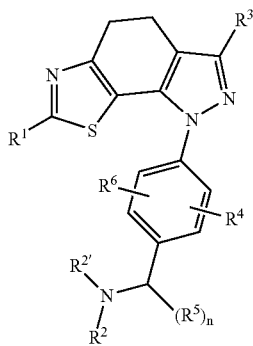

(1A)

wherein the substituents are defined as in claim 1.

3. A compound according to claim 1 or 2, wherein $R^3$ denotes 5-6 membered heteroaryl, optionally substituted by one or more identical or different $R^c$ and/or $R^b$.

4. A compound according to claim 1, wherein $R^3$ denotes unsubstituted pyridyl.

5. A compound according to claim 1, wherein $R^3$ denotes unsubstituted pyridin-3-yl.

6. A compound according to claim 1, wherein $R^1$ is selected from among —NHC(O)$R^a$, —NHC(O)O$R^a$ and —NHC(O)N$R^a R^a$.

7. A pharmaceutical composition containing as active substance one or more compounds of general formula (1) according to claim 1 or the pharmacologically effective salts thereof, optionally in combination with conventional excipients and/or carriers.

8. A pharmaceutical composition comprising a compound of formula (1) according to claim 1 and at least one other cytostatic or cytotoxic active substance, different from formula (1), as well as optionally the pharmacologically acceptable salts thereof.

9. A method for preparing a medicament for the treatment of colon cancer, lung cancer or prostate cancer, which comprises bringing together a compound of formula (1) according to claim 1 together with conventional excipients and/or carriers suitable for providing a medicament.

10. A method for the treatment of colon cancer, lung cancer or prostate cancer, which comprises administering a compound of formula (1) according to claim 1 to a patient in need thereof.

* * * * *